United States Patent
Wiig et al.

(10) Patent No.: US 8,263,826 B2
(45) Date of Patent: Sep. 11, 2012

(54) NEMATODE INDUCIBLE PLANT MTN3-LIKE GENE PROMOTORS AND REGULATORY ELEMENTS

(75) Inventors: Aaron Wiig, Chapel Hill, NC (US); Xiang Huang, Apex, NC (US); Sumita Chaudhuri, Cary, NC (US)

(73) Assignee: BASF Plant Science GmbH (DE)

( * ) Notice: Subject to any disclaimer, the term of this patent is extended or adjusted under 35 U.S.C. 154(b) by 469 days.

(21) Appl. No.: 12/522,292

(22) PCT Filed: Feb. 4, 2008

(86) PCT No.: PCT/EP2008/051328
§ 371 (c)(1),
(2), (4) Date: Jul. 7, 2009

(87) PCT Pub. No.: WO2008/095887
PCT Pub. Date: Aug. 14, 2008

(65) Prior Publication Data
US 2010/0005544 A1    Jan. 7, 2010

Related U.S. Application Data

(60) Provisional application No. 60/899,714, filed on Feb. 6, 2007.

(51) Int. Cl.
*C12N 15/63* (2006.01)
*C12N 15/82* (2006.01)
*A01H 1/00* (2006.01)
(52) U.S. Cl. .................. 800/287; 800/278; 536/24.1
(58) Field of Classification Search ............... None
See application file for complete search history.

(56) References Cited

U.S. PATENT DOCUMENTS

| 7,439,348 B2 * | 10/2008 | Diehn et al. ........... 536/24.1 |
| 2006/0021966 A1 | 9/2006 | Hu et al. |
| 2009/0093620 A1 * | 4/2009 | Kovalic et al. ........ 536/23.1 |

FOREIGN PATENT DOCUMENTS
WO    WO 98/31822    7/1998

OTHER PUBLICATIONS

Gamas Pascal et al, "Use of a Subtractive Hybridizatin Approach to Identify New Medicago Truncatula Genes Induced During Root Nodule Development, Molecular Plant", vol. 9, No. 4,1996, pp. 233-242.

* cited by examiner

*Primary Examiner* — Li Zheng

(57) ABSTRACT

The invention provides promoter polynucleotides that are root-preferred and/or induced by parasitic nematodes. The promoter polynucleotides of the invention are useful for controlling expression of nucleic acids of interest in plant roots.

10 Claims, 16 Drawing Sheets

Figure 1: Sequence of *A. thaliana* promoter region of locus At1g21460 (pWT128) (SEQ ID NO:1). A TATA box is localized at base pair 830 to base pair 836 and is marked in bold.

```
  1 CTCCGGTTAA AATGATCATG AATGAACCGA TATGGTTTGG GTAAAGCTGA
 51 ATAAGCTAAC TCGTGGTGAC TAGAAAACAT TCCAAAAAGA TCACTCACTA
101 TACTAAAAAG TATATCCTGC GGCTGTGGTT CAACGGTATA GAATAACTGA
151 AATTTAGTGA AACTTATTGG TGCCCTTAAA TAAACTTGAC AGTTTGTTAG
201 GTTTGGTTTC GCTTATGTAA CCAGAAACTT CCTAAACTGT CAAATTTTAT
251 CTAGAATCTC TATTAAAGAG GGCAACGAAA AAAAAAAGT AACACATCAT
301 GGAGAAGATG AACCACTAGC CACTGCCCCG CAGAAAATAC AGGCTCGGGC
351 CTCGAGTCAC ATATCAACGT CAAGCCCAGA ACACTCTGGC TTGTTCAGAG
401 CTACTTTTAG TATCAAACAA AAAACAAAAG AAGAAAGAC ATTGCTCTTT
451 TTAGGTGTTT ATTTCATTTT TAAGTATTTA ACCATATCTC TATAACTATC
501 TACAAAAGAA ACGTCGATCC AAAGAGTCAG GTTCACCTCT CGAGGACGTA
551 AAAACAAGTA ACAGATAAAA AACCTCGTTC CAAAAATTAA TTTGGTATCA
601 AGAAAAAATC TGTATATATA CACTAGAATT CAAAATCATG GGAACTTTTT
651 TTTTTTATAT AAGAAATAAC TCAATTAACT CAAATTTAAA ACTTAGGTTT
701 TCTCAAAACA TTAGTTCTTA ACCATAACTT TTTTTCAAA TTTTATTCAT
751 ACTACAAAAA TTAATAACAG AACCATGTAT TTTTAAAATT TAATATTTAA
801 TACCATTATT TCATAATTTA TTATACTTTT ATTAATTTTG TAATTATTGG
851 TGTTCCACAG TGAAGCGGTT AACACACGCT GAATCTCGAT ATATATACGC
901 TTGCCGATAG AAAACACTTA GCTCATATTC TCTCACTTTC TCTCTCAGCT
951 TACGAACAAG AAAAAAAGAA GAATCTTTAG CCACCTTTGA GATCAAAA
```

Figure 2: Sequence of *A. thaliana* promoter region of locus At5g53190 (SEQ ID NO:2).

```
   1 CGACTGTCTC ATCATTTGTG ATTTTTTTTT GCCAGTACTT TATTTTTTTT
  51 GGTAAACTAG ATTGGTCTTA TAACTTATAA GTTATAACAA AATCACATCC
 101 CTCTGTAAAT TTATTTATTT TAACTTTAAC CAAAAAATCA AAAGAATAAG
 151 TTGTGCTGTG TTGAGGACAA ATTTTATAAT AAAGAAATAA GGACACGAAG
 201 GAAGAATGGA AGTCCTTGCT AGTTGGTGCC ATTTCCAATA CGATTCCAAC
 251 AACTTAGCCA ACTTTTTTTT TTTTTTTTTT TTTTGATAAA GAACACCTTA
 301 GCCAACTTAC GAAAAGTTTC TAACTCTTTC GTTCTTTATT AGTTCTATAT
 351 GTATTAATGC ATGCATTATT GTGACCAAAA AGTATATATT AAATAAAAAA
 401 TGTATATTTT CATGTAATTT TGTTTGTAAT ATTATTTATT TTAGTTTTAT
 451 AAATTCACCG TATTCTATTA GTTCGCTAGG TTCTTGAAAC TCAAAATTTG
 501 ATTCTTGAGT GATATATGGT AATCTAGCAA CTCGAATTAG CCTGTAAATT
 551 AATTTAGAAC AATGTAAAGA TTTCATGTTT TTACGTATAA ATTACATGTT
 601 TGCAAATTAA TTAGTTTGGA TTTTGGTATA TAAATGAGGA TATTTTCATT
 651 CATTTAAGTG TTTTGATGTT GAGAAAACAT AGGTATAAAT GATGAATATA
 701 TAACACCAAC ATCATAATTG TTAGTAAATA TTCATTTGAA AAGAGTGAGA
 751 TCAGAAATTG ATTGATAAGG AAGAGACAAT ACAAAAGAGA TGGAAAATGA
 801 ACTAAGTAAA CCATAAGCAT AACTGGATGT GCATTTCAAG CATAATTTGG
 851 CTCAAAACTA AATTTATAAT TAAAATAGAT AATCCTAATT TTTTGACAAG
 901 ATTTTTTTTT TGTTGAGAAA ATGTTTATAA TATACAAAGT TCTTGATAAA
 951 GGACACTAGT TTCACACCCC ACGTGTTGCT AACCGGCCAC CACAAAGCTA
1001 ACTTAAAAAT GTTTTAACT TTTTTAATTG GAGTTCCTTT TTATCTCCAT
1051 GCATTATTAT CATTTCTAT TATATATTCC ATAAGCACTT AAACAAATCA
1101 GTCTTCTTTA TTCGATTCGG AATTTAATGT GATACAAACA AAATAATCAA
1151 AGTTTTTGTG TGTATATCCG TTTAAAAAAA GGGAGATTTG TGTGTACGAT
1201 TTGGATCAAG CCTTTTTGCG CATCAAAATT GTCACTTGCA GACGTTAATG
1251 TGCCCGTTAG ACCTTACAA TCTATTAAAC TAAATAATTT AAAAAATTTC
1301 TATTACTGGA TATATATATA TATATATATA TAAACGTTA TAATCAGGTA
1351 AAATTACTTT CGTAAAAACA AAAACAAAA AATGATTTAC AAATTTGGTT
1401 TTGTAAGATA TATATATATA TATATATATA TATATGCGTT TGTAATTTGG
1451 GATGGAATGG TTGCTAATAG GTTGTTGAAT CACATAATTT GTGTGATATA
1501 TCATCTAGTG TTATACGTGT ATATAAGTTT GTGTAAGACA TTGTATATAT
1551 AAACAACTTA ATCTCCACAC ACGTCTAATA ATGTCATATA TATGGTCTGA
1601 TAACTCCAAG AACTTGAAAT TAGATTTAGT AAACTCAAGA AATGAACAAC
1651 CATCTTTCTA GGTTCGTTTC TAGTTAATGA AACATCCGTG TATGAAAATT
1701 ATATGTTATT CTAAAATTTC CAGTAGTTTT TCTAATTCAA GCTTGGTCTC
1751 TATGTTTTAG AAAAAAGAA AAACTTAGAG AAGCAATTGT TATTTATCTC
1801 ATCACACCAA TATAATTTTT GGAACCAAAT TGTTAAATTA CCAAATGTCC
1851 CAAACTTGTG ATCAAATTTA GATGATTATT TTTAAATGAA CATTAAAGAA
1901 AAACTATTAT ATATATACAC ACCCATTATA GACGTAACTC TACTGCTTCC
1951 AACTTTTCCC TAATCTTTGT TCTTCCGGCC AATCAA
```

Figure 3: Sequence of *Glycine max* promoter region of the gene corresponding to cDNA clone 47116125 contained in pAW222qcz referred to as p-47116125 (SEQ ID NO:3). A TATA box localized at base pair 513 to base pair 519 and is marked in bold.

```
  1 GAAGCCACGT CATGAAGAGT ATATCATTTC AGTAATGTTT TGAGACGCCT
 51 CTATAATGCT TTACCAACAA AACAAAACAA AAAAAAGAAC ATTTGAAACC
101 ATTTGTATTA AAAAAAAAAA GGTATATTAG GCCATAATAT TATAGGTAAC
151 ATGAAATATC AAATGACACG CAAGAGTTTT GTCAAAAATG AAACCATCAC
201 ACATCAGAGA TTATGGCAAA TAATGTTTTG TGTGTCTCTT GCTTCACCCA
251 TAACATAAGC CTCTATAACT GGAGAGAAGA AAAAAAAAAG TGGAGGGGCT
301 AGGGTGGGAA TTTGGAAGAA TACAGTTATA TTGAGCATTG AGCAAGTTGA
351 TAGAAAGCTT CTCAATTTGT ACAAAATTTG CATCCACATG ATTATTAAAG
401 ACGTAGACAG CACTTCTTCC TTCTTTTTTT CTATAAGTTT CTTATATATT
451 GTTCTTCATG TTTTAATATT ATTACTTTAT GTACGCGTCT AACAGTAGTC
501 CTCCCAAACT GCTATAAATA GAGCCTCTTC AACGCACCTC TTGGCAGTAC
551 AAAAATTATT CATCTCTTCT AAGTTCTAAT TTTCTAAGCA TTCAGTAAAA
601 GAACTAACC
```

Figure 4: sequence of *Glycine max* cDNA clone 47116125. The orf start codon is in bold from bases 23-25. The orf stop codon is in bold and italic from bases 785-787. The complete orf spans from bases 23-787.

```
  1  GCATTCAGTA AAAGAACTAA ACATGGCAGA GACCATTCGT TTGGCTGTTG
 51  CTGTTCTTGG CAATGCAGCC TCAGTTGCCC TTTATGCTGC ACCAATGGTT
101  ACCTTTAGAA GAGTTATAAG GAAGAAAAGC ACAGAGGAGT TTTCATGCTT
151  TCCTTACATC ATTGGCCTCT TGAATTGTCT CCTTTTCACT TGGTACGGTT
201  TGCCTGTTGT GAGTTACAAG TGGGAAAATT TCCCTCTCGT CACAGTTAAT
251  GGAGTTGGTA TTGTTCTCGA GTTATCCTAT GTTCTCATTT ACTTCTGGTA
301  TGCTTCAGCC AAAGGAAAGG TGAAGGTAGC CATGACTGCA ATACCAGTTT
351  TGCTGGTGTT CTCTATAATT GCTGCAGTGT CAGCTTTTGC ATTCCATGAT
401  AATCATCACC GGAAGCTTCT CGTAGGTAGC ATCGGCTTAG GTGTTTCAGT
451  AACAATGTAT GGATCCCCTT TGATTGTAAT GAAGAAAGTT ATACAAACCA
501  AGAGTGTGGA ATTCATGCCA CTACCGTTAT CCATGTGCTC ATTTTTAGCC
551  ACTGTTCTCT GGCTGATTTA TGGACTTCTC ATTCGTGATA TATTCGTTGC
601  GGGTCCTAGT GCGGTTGGAA CTCCCTTGGG GATCTTGCAA CTTGTACTTT
651  ACTGTAAATA CCGAAAAGGG AGTGTTGTGG AGGATCCAAG TAAGGGGGAC
701  CTTGAGAAGG GTAACTTGGA GAAGGTGGAA ATGGAAATTG GGAAAGTGGA
751  AATGAATGTC ACGAATCACA TGAACGGACA CTCG***TGA***ACA ATGCGTCTAA
801  GGGGAAAGAT TGAAGATTAC AGAATGTTCT ATTCAGATTC CTTCTTTTA
851  TGTTTATTT CCTTTATTTT AAGACAAAAT GATCCCCCCT TAGCTTTGGT
901  TGTATTGCTC ACATATAAAT TAAGTTATAT TACTTCCCAA AAAAAAAAAA
951  AAAAAA
```

Figure 5: Sequence alignment of the amino acid sequences of *Glycine max* cDNA clone 47116125 (SEQ ID NO:5), *A. thaliana* locus At1g21460 (SEQ ID NO:6), and *A. thaliana* locus At5g53190 (SEQ ID NO:7).

```
                        1                                                 50
47116125       (1)   MAETIRLAVAVLGNAASVALYAAPMVTFRRVIRKKSTEEFSCFPYIIGLL
At1g21460      (1)   -MNIAHTIFGVFGNATALFLFLAPSITFKRIIKNKSTEQFSGIPYPMTLL
At5g53190      (1)   MGDKLRLSIGILGNGASLLLYTAPIVTFSRVFKKKSTEEFSCFPYVMTLF 51                                                100
47116125      (51)   NCLLFTWYGLPVVSYKWENFPLVTVNGVGIVLELSYVLIYFWYASAKGKV
At1g21460     (50)   NCLLSAWYGLPFVS--KDNTLVSTINGTGAVIETVYVLIFLFYAPKKEKI
At5g53190     (51)   NCLIYTWYGLPIVSHLWENLPLVTINGVGILLESIFIFIYFYYASPKEKI 101                                                150
47116125     (101)   KVAMTAIPVLLVFSIIAAVSAFAFHDNHHRKLLVGSIGLGVSVTMYGSPL
At1g21460     (98)   KIFGIFSCVLAVFATVALVSLFALQGN-GRKLFCGLAATVFSIIMYASPL
At5g53190    (101)   KVGVTFVPVIVGFGLTTAISALVFDDHRHRKSFVGSVGLVASISMYGSPL 151                                                200
47116125     (151)   IVMKKVIQTKSVEFMPLPLSMCSFLATVLWLIYGLLIRDIFVAGPSAVGT
At1g21460    (147)   SIMRLVVKTKSVEFMPFFLSLFVFLCGTSWFVYGLIGRDPFVAIPNGFGC
At5g53190    (151)   VVMKKVIETRSVEYMPFYLSFFSFLASSLWLAYGLLSHDLFLASPNMVAT 201                                                250
47116125     (201)   PLGILQLVLYCKYRKG-----SVVEDPSKGDLEKGNLEKVEMEIGKVEMN
At1g21460    (197)   ALGTLQLILYFIYCGNK---------GEKSADAQKDEKSVEMKDDEKKQN
At5g53190    (201)   PLGILQLILYFKYKNKKDLAPTTMVITKRNDHDDKNKATLEFVVDVDRNS 251       263
47116125     (246)   VTNHMNGHS----
At1g21460    (238)   VVNGKQDLQV---
At5g53190    (251)   DTNEKNSNNASSI
```

Figure 6: Sequence of pAW127 genome walking derived sequence (SEQ ID NO:8). The start codon for the coding sequence of 47116125 marked in bold and is located from bp 660-662. There is a stop codon upstream of this start codon in the same frame marked in bold and italic beginning at bp 627. The promoter sequence cloned into pAW222qcz is represented by bp 51 to 659.

```
   1 ACTATAGGGC ACGCGTGGTC GACGGCCCGG GCTGGTATCT CTACAAAATG
  51 GAAGCCACGT CATGAAGAGT ATATCATTTC AGTAATGTTT TGAGACGCCT
 101 CTATAATGCT TTACCAACAA AACAAAACAA AAAAAAGAAC ATTTGAAACC
 151 ATTTGTATTA AAAAAAAAAA GGTATATTAG GCCATAATAT TATAGGTAAC
 201 ATGAAATATC AAATGACACG CAAGAGTTTT GTCAAAATG AAACCATCAC
 251 ACATCAGAGA TTATGGCAAA TAATGTTTTG TGTGTCTCTT GCTTCACCCA
 301 TAACATAAGC CTCTATAACT GGAGAGAAGA AAAAAAAAAG TGGAGGGGCT
 351 AGGGTGGGAA TTTGGAAGAA TACAGTTATA TTGAGCATTG AGCAAGTTGA
 401 TAGAAAGCTT CTCAATTTGT ACAAAATTTG CATCCACATG ATTATTAAAG
 451 ACGTAGACAG CACTTCTTCC TTCTTTTTTT CTATAAGTTT CTTATATATT
 501 GTTCTTCATG TTTTAATATT ATTACTTTAT GTACGCGTCT AACAGTAGTC
 551 CTCCCAAACT GCTATAAATA GAGCCTCTTC AACGCACCTC TTGGCAGTAC
 601 AAAAATTATT CATCTCTTCT AAGTTCTAAT TTTCTAAGCA TTCAGTAAAA
 651 GAACTAACCA TGGCAGAGAC CATTCGCTTG GGTGTTGCTG TTCTTGGTAC
 701 TTCTTCGTTC ATTCATTCCT TAGCTTGAA CGTATAGGGT GATTAATTAT
 751 TATTCATTAT TTGAGTCTTC AAAAAAAGTG ACTCATTAGT ACCACTGTTT
 801 GTTTTTTTTT TTCTTGCAGG CAATGCAGCC TCAGTTGCCC TTTATGCTGC
 851 ACCAATGTAT GTTACATGTT ACATATATAA TAACATTGCT GCCCAAATGT
 901 CCTCCCCTTT AGAGAATGAA TAAAGTGCTG AACGCTTTTT CATGCTTTTC
 951 ATGTTCCAGG GTTACCTTTA GAAGAGTTAT AAGGAAGAAA AGCACAGAGG
1001 AGTTTCATG CTTTCCTTAC ATCATTGGCC TCTTGAACTG TCTCCTTTTC
1051 ACTTGGTACG GTTTGCCTAT TGTTAGCTAC AAGTGGGAAA ATTTCCCTCT
1101 CGTCACAGTT AATGGAGTTG GTATTGT
```

Figure 7a:

Sequence alignment of *G. max* cDNA clone 47116125 (SEQ ID NO:4) and genome walking derived *G. max* sequence contained in pAW127 (SEQ ID NO:8) targeting cDNA clone 47116125. The ATG start codon of *G. max* cDNA clone 47116125 (SEQ ID NO:4) starts at bp 660 of pAW127 sequence. A promoter polynucleotide of 609 bp is described by SEQ ID NO:3 and is derived from bases 51 to 659 of pAW127 sequence (SEQ ID NO:8). Sequence mismatches between pAW127 sequence and 47116125 cDNA sequence are marked with an asterisk.

```
pAW127      #1      ACTATAGGGC ACGCGTGGTC GACGGCCCGG GCTGGTATCT CTACAAAATG pAW127      #51     GAAGCCACGT CATGAAGAGT ATATCATTTC AGTAATGTTT TGAGACGCCT pAW127      #101    CTATAATGCT TTACCAACAA AACAAAACAA AAAAAAGAAC ATTTGAAACC pAW127      #151    ATTTGTATTA AAAAAAAAAA GGTATATTAG GCCATAATAT TATAGGTAAC pAW127      #201    ATGAAATATC AAATGACACG CAAGAGTTTT GTCAAAAATG AAACCATCAC pAW127      #251    ACATCAGAGA TTATGGCAAA TAATGTTTTG TGTGTCTCTT GCTTCACCCA pAW127      #301    TAACATAAGC CTCTATAACT GGAGAGAAGA AAAAAAAAAG TGGAGGGGCT pAW127      #351    AGGGTGGGAA TTTGGAAGAA TACAGTTATA TTGAGCATTG AGCAAGTTGA pAW127      #401    TAGAAAGCTT CTCAATTTGT ACAAAATTTG CATCCACATG ATTATTAAAG pAW127      #451    ACGTAGACAG CACTTCTTCC TTCTTTTTTT CTATAAGTTT CTTATATATT pAW127      #501    GTTCTTCATG TTTTAATATT ATTACTTTAT GTACGCGTCT AACAGTAGTC pAW127      #551    CTCCCAAACT GCTATAAATA GAGCCTCTTC AACGCACCTC TTGGCAGTAC

47116125    #1                                                CCA TTCACTAAAA
pAW127      #601    AAAAATTATT CATCTCTTCT AAGTTCTAAT TTCTAAGCA TTCAGTAAAA

47116125    #14     GAACTAAACA TGGCAGAGAC CATTCGTTTG GCTGTTGCTG TTCTT:::::
pAW127      #651    GAACTAACCA TGGCAGAGAC CATTCGCTTG GGTGTTGCTG TTCTTGGTAC
                             *                    *        *

47116125    #64     :::::::::: :::::::::: :::::::::: :::::::::: ::::::::::
pAW127      #701    TTCTTCGTTC ATTCATTCCT TAGCTTTGAA CGTATAGGGC GATCAATTAT

47116125    #114    :::::::::: :::::::::: :::::::::: :::::::::: ::::::::::
pAW127      #751    TATTCATTAT TTGAGTCTTC AAAAAAAGTG ACTCATTAGT ACCACTGTTT
```

Figure 7b

```
47116125    #164     ::::::::::  ::::::::GG  CAATGCAGCC  TCAGTTGCCC  TTTATGCTGC
pAW127      #801     GTTTTTTTT   TTCTTGCAGG  CAATGCAGCC  TCAGTTGCCC  TTTATGCTGC

47116125    #214     ACCAATG:::  ::::::::::  ::::::::::  ::::::::::  ::::::::::
pAW127      #851     ACCAATGTAT  GTTACATGTT  ACATATATAA  TAACATTGCT  GCCCAAATGT

47116125    #264     ::::::::::  ::::::::::  ::::::::::  ::::::::::  ::::::::::
pAW127      #901     CCTCCCCTTT  AGAGAATGAA  TAAAGTGCTG  AACGCTTTTT  CATGCTTTTC

47116125    #314     ::::::::::  GTTACCTTTA  AAGAGTTAT   AAGGAAGAAA  AGCACAGAGG
pAW127      #951     ATGTTCCAGG  GTTACCTTTA  AAGAGTTAT   AAGGAAGAAA  AGCACAGAGG

47116125    #364     AGTTTTCATG  CTTTCCTTAC  ATCATTGGCC  TCTTGAATTG  TCTCCTTTTC
pAW127      #1001    AGTTTTCATG  CTTTCCTTAC  ATCATTGGCC  TCTTGAACTG  TCTCCTTTTC
                                                                *

47116125    #414     ACTTGGTACG  GTTTGCCTGT  TGTGAGTTAC  AAGTGGGAAA  ATTTCCCTCT
pAW127      #1051    ACTTGGTACG  GTTTGCCTAT  TGTTAGCTAC  AAGTGGGAAA  ATTTCCCTCT
                                         *     *  *

47116125    #464     CGTCACAGTT  AATGCAGTTC  CTATTGTTCT  CCACTTATCC  TATCTTCTCA
pAW127      #1101    CGTCACAGTT  AATGGAGTTG  GTATTGT

47116125    #514     TTTACTTCTG  GTATGCTTCA  GCCAAAGGAA  AGGTGAAGGT  AGCCATGACT

47116125    #564     GCAATACCAG  TTTTGCTGGT  GTTCTCTATA  ATTGCTGCAG  TGTCAGCTTT

47116125    #614     TGCATTCCAT  GATAATCATC  ACCGGAAGCT  TCTCGTAGGT  AGCATCGGCT

47116125    #664     TAGGTGTTTC  AGTAACAATG  TATGGATCCC  CTTTGATTGT  AATGAAGAAA

47116125    #714     GTTATACAAA  CCAAGAGTGT  GGAATTCATG  CCACTACCGT  TATCCATGTG

47116125    #764     CTCATTTTTA  GCCACTGTTC  TCTGGCTGAT  TTATGGACTT  CTCATTCGTG

47116125    #814     ATATATTCGT  TGCGGGTCCT  AGTGCGGTTG  GAACTCCCTT  GGGGATCTTG

47116125    #864     CAACTTGTAC  TTTACTGTAA  ATACCGAAAA  GGGAGTGTTG  TGGAGGATCC

47116125    #914     AAGTAAGGGG  GACCTTGAGA  AGGGTAACTT  GGAGAAGGTG  GAAATGGAAA

47116125    #964     TTGGGAAAGT  GGAAATGAAT  GTCACGAATC  ACATGAACGG  ACACTCGTGA

47116125    #1014    ACAATGCGTC  TAAGGGGAAA  GATTGAAGAT  TACAGAATGT  CTATTCAGA

47116125    #1064    TTCCTTCTTT  TTATGTTTTA  TTTCCTTTAT  TTTAAGACAA  AATGATCCCC

47116125    #1114    CCTTAGCTTT  GGTTGTATTG  CTCACATATA  AATTAAGTTA  TATTACTTCC

47116125    #1164    CAAAAAAAAA  AAAAAAAA
```

Figure 8: ß-glucuronidase expression patterns of binary vectors pAW222qcz and pWT128 in the soybean hairy root assay set forth in Example 2. Soybean cyst nematode infected hairy roots and control uninfected hairy roots were stained 12 days after SCN inoculation. The following scoring index was used: "-" for no GUS staining, "+" for weak GUS staining, "++" for strong GUS staining.

SCN infected:

| SeqID | Construct | Root tip | Vascular | Cortical | Syncytia |
|---|---|---|---|---|---|
| 1 | PWT128 | - | + | - | + |
| 3 | PAW222qcz | - | ++ | - | ++ |

Control uninfected:

| SeqID | Construct | Root tip | Vascular | Cortical |
|---|---|---|---|---|
| 1 | PWT128 | - | + | - |
| 3 | pAW222qcz | - | ++ | - |

Figure 9: ß-glucuronidase expression patterns of binary vectors pWT128, RTJ113, and RTJ114 in the soybean hairy root assay set forth in Example 4. Soybean cyst nematode infected hairy roots and control uninfected hairy roots were stained 12 days after SCN inoculation. The following scoring index was used: "-" for no GUS staining, "+" for weak GUS staining, "++" for strong GUS staining.

SCN infected:

| SeqID | Construct | Root tip | Vascular | Cortical | Syncytia |
|---|---|---|---|---|---|
| 1 | PWT128 | - | + | - | + |
| 1 | RTJ113 | - | ++ | - | + |
| 1 | RTJ114 | - | ++ | - | + |

Control uninfected:

| SeqID | Construct | Root tip | Vascular | Cortical |
|---|---|---|---|---|
| 1 | PWT128 | - | + | - |
| 1 | RTJ113 | - | ++ | - |
| 1 | RTJ114 | - | ++ | - |

Figure 10: ß-glucuronidase expression patterns of binary vectors pAW222qcz, RTJ117, and RTJ118 in the soybean hairy root assay set forth in Example 4. Soybean cyst nematode infected hairy roots and control uninfected hairy roots were stained 12 days after SCN inoculation. The following scoring index was used: "-" for no GUS staining, "+" for weak GUS staining, "++" for strong GUS staining.

SCN infected:

| SeqID | Construct | Root tip | Vascular | Cortical | Syncytia |
|---|---|---|---|---|---|
| 3 | PAW222qcz | - | ++ | - | ++ |
| 3 | RTJ117 | - | ++ | - | ++ |
| 3 | RTJ118 | - | + | - | ++ |

Control uninfected:

| SeqID | Construct | Root tip | Vascular | Cortical |
|---|---|---|---|---|
| 3 | PAW222qcz | - | ++ | - |
| 3 | RTJ117 | - | ++ | - |
| 3 | RTJ118 | - | + | - |

Figure 11: PCR primers used to obtain the promoter polynucleotides of SEQ ID NO:1, SEQ ID NO:2, SEQ ID NO:3, the 500 bp deletion of *A. thaliana* promoter of locus At1g21460 (SEQ ID NO:1), the 251 bp deletion of *A. thaliana* promoter of locus At1g21460 (SEQ ID NO:1), the 410 bp deletion of *Glycine max* promoter p-47116125 (SEQ ID NO:3), and the 210 bp deletion of *Glycine max* promoter p-47116125 (SEQ ID NO:3).

| Common primer | SEQ ID NO | Seq. 5' to 3' |
|---|---|---|
| At1g21460prF | 9 | AACTGCAGCTCCGGTTAAAATGATCAT |
| At1g21460prR | 10 | AAGGCGCGCCTTTTGATCTCAAAGGTGGCT |
| At5g53190prF | 11 | AATTAATTAACGACTGTCTCATCATTTGTG |
| At5g53190prR | 12 | AAGGCGCGCCTTGATTGGCCGGAAGAACAAAG |
| AP1 | 13 | GTAATACGACTCACTATAGGGC |
| AP2 | 14 | ACTATAGGGCACGCGTGGT |
| 47116125GW | 15 | CACCAGCAAAACTGGTATTGCAGTCATGG |
| 47116125GWnest | 16 | ACAATACCAACTCCATTAACTGTGACGAGAG |
| 47116125prF | 17 | CTGCAGGAAGCCACGTCATGAAGAG |
| 47116125prR | 18 | GGCGCGCCGGTTAGTTCTTTTACTGAATGC |
| At1g21460pr499bpF | 19 | ACGTCTGCAGCTACAAAAGAAACGTCGATCC |
| At1g21460pr251bpF | 20 | ACGTCTGCAGCATACTACAAAAATTAATAACAGAAC |
| At1g21460prR2 | 21 | ACGTGGCGCGCCTTTTGATCTCAAAG |
| 47116125pr410bpF | 22 | GCATCTGCAGCACATCAGAGATTATG |
| 47116125pr210bpF | 23 | GCATCTGCAGGACGTAGACAGCACTTC |
| 47116125prR2 | 24 | GCTTGACGTCGGTTAGTTCTTTTACTG |

Figure 12: Table showing general sequence formulas (formula 1 and formula 2) of sequence elements identified in minimal promoter polynucleotide fragments.

| sequence element | general formula 1 for sequence element | SEQ ID NO: | general formula 2 for sequence element | SEQ ID NO: |
|---|---|---|---|---|
| element 1 | wndwmvnkmdagaan | 25 | wraaavttwdagaad | 34 |
| element 2 | nnwmwhmwsttannnnn | 26 | rramwacwsttakmynh | 35 |
| element 3 | wmwactdttdnnh | 27 | wmwactdttakwh | 36 |
| element 4 | nbnntatawawhnnn | 28 | hydhtatawatabrs | 37 |
| element 5 | hawhttawtnn | 29 | waawttawtmh | 38 |
| element 6 | dnwrnnnttaadwdhdn | 30 | wnwrdtwttaawwdwwv | 39 |
| element 7 | nnaamwnwnndnwnwnrrd | 31 | kraaatwakrrywtwraak | 40 |
| element 8 | nnnatdattan | 32 | ymratdattan | 41 |
| element 9 | dwwdwhwaamwbwanwd | 33 | wattwwtaaawgwayaw | 42 |

Letter symbols used as abbreviations for alternative nucleotides

| symbol | nucleotide alternatives |
|---|---|
| a | a (adenin) |
| g | g (guanin) |
| c | c (cytosin) |
| t | t (thymin) |
| r | g or a |
| y | t or c |
| m | a or c |
| k | g or t |
| s | g or c |
| w | a or t |
| b | g or c or t |
| d | a or g or t |
| h | a or c or t |
| v | a or g or c |
| n | a or g or c or t |

Figure 13: General sequence for minimal promoter polynucleotide fragment of *A. thaliana* promoter region of locus At1g21460 (pWT128) (SEQ ID NO:43) and table showing 16 sequence elements contained in SEQ ID NO. 43.

```
  1 CAAAAATTAA TAACAGANNN NTGTATTTTT AAAATTTAAT ATTTAATACC
 51 ATTATTTCAT AATTTATTAT ACTTTATTA ATTTTGTAAT TATTGGNNNN
101 NNNNNNNNNN NNNNNNNNNN NNNNNNNNNN NTCGATATAT ATACGCNNNN
151 NNNNAGAAAA CACTTAGCTC ANATTCTCTC ACTTTCTNNN
```

| element (No.) | start position (nucleotide) | end position (nucleotide) | plus strand (+) or minus strand (-) |
|---|---|---|---|
| element 5 | 3 | 13 | + |
| element 6 | 1 | 17 | - |
| element 6 | 22 | 38 | + |
| element 5 | 32 | 42 | + |
| element 6 | 30 | 46 | - |
| element 6 | 37 | 53 | - |
| element 7 | 41 | 59 | - |
| element 5 | 60 | 70 | + |
| element 3 | 68 | 80 | + |
| element 9 | 67 | 83 | - |
| element 5 | 75 | 85 | - |
| element 8 | 86 | 96 | - |
| element 4 | 132 | 146 | + |
| element 2 | 155 | 171 | + |
| element 1 | 173 | 187 | - |

Figure 14: General sequence for minimal promoter polynucleotide fragment of *A. thaliana* promoter region of locus At5g53190 (SEQ ID NO:44) and table showing 9 sequence elements contained in SEQ ID NO. 44

```
  1 ATTCTAAAAT TTCCANNNNN NNNNNNNNNN NNNNNNNNNN NNNNNNNNNN
 51 NNNNNNNNNN NAAAAACTTA GAGAAGNNNN NNNNNNNNNN NNNNNNNNNN
101 NNNNNNNNNN NNNNNNNNNN NNNNNNNNNN NNNNNNNNNN NNNNNNNNNN
151 NNNNNNNNNN NTAGATGATT ATTTTTAAAT GAACATTAAA GAAAAACTAT
201 TATATATATA C
```

| element (No.) | start position (nucleotide) | end position (nucleotide) | plus strand (+) or minus strand (-) |
|---|---|---|---|
| element 1 | 1 | 15 | - |
| element 1 | 62 | 76 | + |
| element 8 | 162 | 172 | + |
| element 6 | 168 | 184 | + |
| element 9 | 170 | 186 | + |
| element 1 | 180 | 194 | + |
| element 2 | 191 | 207 | + |
| element 3 | 193 | 205 | + |
| element 4 | 197 | 211 | + |

Figure 15: General sequence for minimal promoter polynucleotide fragment of *Glycine max* promoter region of the gene corresponding to cDNA clone 47116125 (SEQ ID NO:45) and table showing 7 sequence elements contained in SEQ ID NO. 45

```
  1 TTTCTATAAG TTTCTNNNNN NNNNNNNNNN NNNNNNNAAT ATTATTACNN
 51 NNNNNNNGCG TCTAACAGTA GTCCNNNNNN NCTGCTATAA ATAGAGNNNN
101 NNNNNNNNNN NNNNNNNNNN NNNNAAAATT ATTCANNNNT TCTAAGTTCT
151 AATTTTC
```

| element (No.) | start position (nucleotide) | end position (nucleotide) | plus strand (+) or minus strand (-) |
|---|---|---|---|
| element 1 | 1 | 15 | - |
| element 5 | 38 | 48 | + |
| element 2 | 58 | 74 | - |
| element 3 | 60 | 72 | - |
| element 4 | 82 | 96 | + |
| element 5 | 125 | 135 | + |
| element 7 | 139 | 157 | - |

NEMATODE INDUCIBLE PLANT MTN3-LIKE GENE PROMOTORS AND REGULATORY ELEMENTS

CROSS REFERENCE TO RELATED APPLICATIONS

This application is a national stage application under 35 U.S.C. §371 of PCT/EP2008/051328, filed Feb. 4, 2008, which claims benefit of U.S. provisional application Ser. No. 60/899,714, filed Feb. 6, 2007. The entire contents of each of the above-identified applications are incorporated herein by reference.

FIELD OF THE INVENTION

This invention relates to promoter and regulatory element sequences that regulate transcription of genes similar to MtN3-like genes. The promoters of MtN3-like genes of the invention are useful for controlling transcription of any nucleic acid of interest in plant roots. In particular, the promoters of the invention may be used to control transcription of nucleic acids encoding agents that disrupt the formation or maintenance of the feeding site, disrupt the growth and/or reproduction of plant parasitic nematodes, that confer or improve plant resistance to plant parasitic nematodes, or that are toxic to plant parasitic nematodes to reduce crop destruction.

BACKGROUND OF THE INVENTION

Nematodes are microscopic roundworms that feed on the roots, leaves and stems of more than 2,000 row crops, vegetables, fruits, and ornamental plants, causing an estimated $100 billion crop loss worldwide. A variety of parasitic nematode species infect crop plants, including root-knot nematodes (RKN), cyst- and lesion-forming nematodes. Root-knot nematodes, which are characterized by causing root gall formation at feeding sites, have a relatively broad host range and are therefore pathogenic on a large number of crop species. The cyst- and lesion-forming nematode species have a more limited host range, but still cause considerable losses in susceptible crops.

Pathogenic nematodes are present throughout the United States, with the greatest concentrations occurring in the warm, humid regions of the South and West and in sandy soils. Soybean cyst nematode (*Heterodera glycines*), the most serious pest of soybean plants, was first discovered in the United States in North Carolina in 1954. Some areas are so heavily infested by soybean cyst nematode (SCN) that soybean production is no longer economically possible without control measures. Although soybean is the major economic crop attacked by SCN, SCN parasitizes some fifty hosts in total, including field crops, vegetables, ornamentals, and weeds.

Signs of nematode damage include stunting and yellowing of leaves, and wilting of the plants during hot periods. However, nematode infestation can cause significant yield losses without any obvious above-ground disease symptoms. The primary causes of yield reduction are due to root damage underground. Roots infected by SCN are dwarfed or stunted. Nematode infestation also can decrease the number of nitrogen-fixing nodules on the roots, and may make the roots more susceptible to attacks by other soil-borne plant pathogens.

The nematode life cycle has three major stages: egg, juvenile, and adult. The life cycle varies between species of nematodes. For example, the SCN life cycle can usually be completed in 24 to 30 days under optimum conditions whereas other species can take as long as a year, or longer, to complete the life cycle. When temperature and moisture levels become favorable in the spring, worm-shaped juveniles hatch from eggs in the soil. Only nematodes in the juvenile developmental stage are capable of infecting soybean roots.

The life cycle of SCN has been the subject of many studies, and as such are a useful example for understanding the nematode life cycle. After penetrating soybean roots, SCN juveniles move through the root until they contact vascular tissue, at which time they stop migrating and begin to feed. With a stylet, the nematode injects secretions that modify certain root cells and transform them into specialized feeding sites. The root cells are morphologically transformed into large multinucleate syncytia (or giant cells in the case of RKN), which are used as a source of nutrients for the nematodes. The actively feeding nematodes thus steal essential nutrients from the plant resulting in yield loss. As female nematodes feed, they swell and eventually become so large that their bodies break through the root tissue and are exposed on the surface of the root.

After a period of feeding, male SCN nematodes, which are not swollen as adults, migrate out of the root into the soil and fertilize the enlarged adult females. The males then die, while the females remain attached to the root system and continue to feed. The eggs in the swollen females begin developing, initially in a mass or egg sac outside the body, and then later within the nematode body cavity. Eventually the entire adult female body cavity is filled with eggs, and the nematode dies. It is the egg-filled body of the dead female that is referred to as the cyst. Cysts eventually dislodge and are found free in the soil. The walls of the cyst become very tough, providing excellent protection for the approximately 200 to 400 eggs contained within. SCN eggs survive within the cyst until proper hatching conditions occur. Although many of the eggs may hatch within the first year, many also will survive within the protective cysts for several years.

A nematode can move through the soil only a few inches per year on its own power. However, nematode infestation can be spread substantial distances in a variety of ways. Anything that can move infested soil is capable of spreading the infestation, including farm machinery, vehicles and tools, wind, water, animals, and farm workers. Seed sized particles of soil often contaminate harvested seed. Consequently, nematode infestation can be spread when contaminated seed from infested fields is planted in non-infested fields. There is even evidence that certain nematode species can be spread by birds. Only some of these causes can be prevented.

Traditional practices for managing nematode infestation include: maintaining proper soil nutrients and soil pH levels in nematode-infested land; controlling other plant diseases, as well as insect and weed pests; using sanitation practices such as plowing, planting, and cultivating of nematode-infested fields only after working non-infested fields; cleaning equipment thoroughly with high pressure water or steam after working in infested fields; not using seed grown on infested land for planting non-infested fields unless the seed has been properly cleaned; rotating infested fields and alternating host crops with non-host crops; using nematicides; and planting resistant plant varieties.

Methods have been proposed for the genetic transformation of plants in order to confer increased resistance to plant parasitic nematodes. U.S. Pat. Nos. 5,589,622 and 5,824,876 are directed to the identification of plant genes expressed specifically in or adjacent to the feeding site of the plant after attachment by the nematode. U.S. Pat. Nos. 5,589,622 and 5,824,876 disclose eight promoters isolated from potato roots infected with *Globodera rostochiensis*: no nematode-inducible promoters from other plant species are disclosed. These promoters are purported to be useful to direct the specific expression of toxic proteins or enzymes, or the expression of antisense RNA to a target gene or to general cellular genes.

U.S. Pat. No. 5,023,179 discloses a promoter enhancer element designated ASF-1, isolated from the CaMV promoter, which is purported to enhance plant gene expression in roots.

U.S. Pat. No. 5,750,386 discloses a deletion fragment of the RB7 root specific promoter of *Nicotiana tabacum*, which is purported to be nematode-responsive.

U.S. Pat. No. 5,837,876 discloses a root cortex specific gene promoter isolated from tobacco and designated TobRD2.

U.S. Pat. No. 5,866,777 discloses a two-gene approach to retarding formation of a nematode feeding structure. The first gene, barnase, is under control of a promoter that drives expression at least in the feeding structure. The second gene, barstar, is under control of a promoter that drives expression in all of the plant's cells except the feeding structure. Feeding site-specific promoters disclosed in U.S. Pat. No. 5,866,777 include truncated versions of the Δ0.3TobRB7 and roIC promoters.

U.S. Pat. No. 5,955,646 discloses chimeric regulatory regions based on promoters derived from the mannopine synthase and octopine synthase genes of *Agrobacterium tumefaciens*, which are purported to be nematode-inducible.

U.S. Pat. No. 6,005,092 discloses the *N. tabacum* endo-1, 4-β-glucanase (Ntce17) promoter.

U.S. Pat. Nos. 6,262,344 and 6,395,963 disclose promoters isolated from *Arabidopsis thaliana*, which are purported to be nematode-inducible.

U.S. Pat. No. 6,448,471 discloses a promoter from *A. thaliana*, which is specific for nematode feeding sites.

U.S. Pat. No. 6,703,541 discloses cloning and isolation of maize peroxidase P7X gene and its promoter, the promoter is purported to be nematode inducible.

U.S. Pat. No. 6,593,513 discloses transformation of plants with barnase under control of the promoter of the *A. thaliana* endo-1,4-β-glucanase gene (cel1) to produce plants capable of disrupting nematode attack.

U.S. Pat. No. 6,906,241 discloses use of the Ntce17 promoter in combination with a heterologous nucleic acid that encodes a nematocidal or insecticidal protein.

U.S. Pat. No. 7,078,589 discloses cloning and isolation of the soybean Pyk20 gene and promoter, which are purported to be induced by SCN infection and to show strong activity in vascular tissues.

U.S. Patent Application Publication No. 2003/0167507 discloses the promoter of soybean isoflavone synthase 1, which is purported to be root specific and inducible in vegetative tissue by parasite attack.

U.S. Patent Application Publication No. 2004/0078841 discloses promoter regions of the TUB-1, RPL16A, and ARSK1 promoters of *Arabidopsis thaliana* and the PSMTA promoter from *Pisum sativum*, all of which are purported to be root-specific.

U.S. Patent Application Publication No. 2004/0029167 discloses a promoter sequence of a class II caffeic acid O-methyltransferase gene from tobacco, which is purported to be inducible in response to mechanical or chemical injury or to aggression by a pathogenic agent.

U.S. Patent Application Publication No. 2005/0262585 discloses a promoter from soybean phosphoribosylformylglycinamidine ribonucleotide synthase and deletion fragments thereof, which are purported to be responsive to nematode infection.

WO 94/10320 discloses the Δ0.3TobRB7 promoter fragment from tobacco and its use with a variety of genes for nematode feeding cell-specific expression.

WO 03/033651 discloses synthetic nematode-regulated promoter sequences designated SCP1, UCP3, and SUP.

WO 2004/029222 and its US counterpart U.S. Patent Application Publication No. 2005/0070697 disclose regulatory regions from the soybean adenosine-5'-phosphate deaminase and inositol-5-phosphatase genes, for use in improving nematode resistance in plants.

None of the above-mentioned root- or feeding-site specific promoters are currently in use in commercial seed containing an anti-nematode transgene. Although the need for such products has long been acknowledged, no one has thus far succeeded in developing nematode-resistant plants through recombinant DNA technology. A need continues to exist for root-specific and/or nematode feeding site-specific promoters to combine with transgenes encoding agents toxic to plant parasitic nematodes.

SUMMARY OF THE INVENTION

The invention provides promoter polynucleotides suitable for use in driving expression of a nucleic acid in plant roots which are susceptible to attack by nematodes. The promoters of the invention are particularly useful for making agricultural crop plants resistant to infestation by nematodes.

In another embodiment, the invention provides a promoter comprising an promoter polynucleotide capable of mediating root-specific and/or nematode-inducible expression, wherein the promoter polynucleotide is selected from the group of polynucleotides consisting of a) a polynucleotide having a sequence as set forth in SEQ ID NO:1, 2, or 3; b) a polynucleotide comprising nucleotides 748 to 998, or nucleotides 500 to 998, or nucleotides 573 to 922 of a polynucleotide having the sequence as set forth in SEQ ID NO:1; c) a polynucleotide comprising nucleotides 1637 to 1989 of a polynucleotide having the sequence as set forth in SEQ ID NO:2; d) a polynucleotide comprising nucleotides 400 to 609, or nucleotides 260 to 609, or nucleotides 200 to 609 of a polynucleotide having the sequence as set forth in SEQ ID NO:3; e) a polynucleotide having at least 70% sequence identity to any of the polynucleotides of a) through d); f) a polynucleotide hybridizing under stringent conditions to any of the polynucleotides of a) through d); and g) a polynucleotide comprising a fragment of at least 50 consecutive nucleotides, or at least 100 consecutive nucleotides, or at least 200 consecutive nucleotides of a polynucleotide having a sequence as set forth in SEQ ID NO:1, 2, or 3, h) a polynucleotide obtained or obtainable from a genomic fragment, comprising a promoter polynucleotide being at least 30% identical to any of the polynucleotides of a) through d), and comprising a polynucleotide coding for a polypeptide sequence, which is at least 80% identical to a sequence as described by SEQ ID NO: 5, SEQ ID NO: 6 or SEQ ID NO: 7. and which is functionally linked to the promoter polynucleotide being at least 30% identical to any of the polynucleotides of a) through d), or i) a polynucleotide being an equivalent fragment of any polynucleotide of a) through f).

In another embodiment, the invention provides a method of down-regulating genes essential for development and maintenance of a nematode feeding site, syncytia, or giant cell, by disrupting the function of promoters of present invention using methods known to those of skill in the art such as antisense or RNAi sequences.

The invention also relates to expression cassettes and transgenic plants which comprise the promoter polynucleotides of the invention, and to methods of controlling parasitic nematode infestations in crops, wherein the methods employ recombinant nucleic acid constructs comprising the promoters of the invention in operative association with a nucleic acid that encodes an agent that disrupts metabolism, growth, and/or reproduction of plant parasitic nematodes, that confers or improves plant resistance to plant parasitic nematodes, or that is toxic to plant parasitic nematodes to reduce crop destruction.

BRIEF DESCRIPTION OF THE DRAWINGS

FIG. 1: Sequence of A. thaliana promoter region of locus At1g21460 (pWT128) (SEQ ID NO:1, TATA box bases 830-836 is in bold).

FIG. 2: Sequence of A. thaliana promoter region of locus At5g53190 (SEQ ID NO:2).

FIG. 3: Sequence of Glycine max promoter region of the gene corresponding to cDNA clone 47116125 (p-47116125) contained in pAW222qcz (SEQ ID NO:3; TATA box bases 513-519 is in bold).

FIG. 4: sequence of Glycine max cDNA clone 47116125 (SEQ ID NO:4). The orf start codon is in bold from bases 23-25. The orf stop codon is in bold and italic from bases 785-787. The complete orf spans from bases 23-787.

FIG. 5: Sequence alignment of the amino acid sequences of Glycine max cDNA clone 47116125 (SEQ ID NO:5), A. thaliana locus At1g21460 (SEQ ID NO:6), and A. thaliana locus At5g53190 (SEQ ID NO:7).

FIG. 6: Sequence of pAW127 genome walking derived sequence (SEQ ID NO:8). The start codon for the coding sequence of 47116125 is marked in bold and is located from bp 660-662. There is a stop codon upstream of this start codon in the same frame marked in bold and italic. The promoter polynucleotide sequence cloned into pAW222qcz is represented by nucleotides from position 51 to 659.

FIGS. 7a-b: Sequence alignment of G. max cDNA clone 47116125 (SEQ ID NO:4) and genome walking derived G. max sequence contained in pAW127 (SEQ ID NO:8) targeting cDNA clone 47116125. The ATG start codon of G. max cDNA clone 47116125 (SEQ ID NO:4) starts at nucleotide position 660 of pAW127 sequence. A promoter polynucleotide of 609 bp is described by SEQ ID NO:3 and is derived from nucleotide position 51 to 659 of pAW127 sequence (SEQ ID NO:8).

FIG. 8: β-glucuronidase expression patterns of binary vectors pAW222qcz and pWT128 in the soybean hairy root assay set forth in Example 3. Soybean cyst nematode infected hairy roots and control uninfected hairy roots were stained 12 days after SCN inoculation. The following scoring index was used: "−" for no GUS staining, "+" for weak GUS staining, "++" for strong GUS staining.

FIG. 9: β-glucuronidase expression patterns of binary vectors pWT128 and the promoter polynucleotide deletion constructs RTJ113 and RTJ114 in the soybean hairy root assay set forth in Example 5. Soybean cyst nematode infected hairy roots and control uninfected hairy roots were stained 12 days after SCN inoculation. The following scoring index was used: "−" for no GUS staining, "+" for weak GUS staining, "++" for strong GUS staining.

FIG. 10: β-glucuronidase expression patterns of binary vectors pAW222qcz and the promoter polynucleotide deletion constructs RTJ117 and RTJ118 in the soybean hairy root assay set forth in Example 5. Soybean cyst nematode infected hairy roots and control uninfected hairy roots were stained 12 days after SCN inoculation. The following scoring index was used: "−" for no GUS staining, "+" for weak GUS staining, "++" for strong GUS staining.

FIG. 11: PCR primers used to obtain the promoters polynucleotides of SEQ ID NO:1, SEQ ID NO:2, SEQ ID NO:3, the 500 bp deletion of A. thaliana promoter of locus At1g21460 (SEQ ID NO:1), the 251 bp deletion of A. thaliana promoter of locus At1g21460 (SEQ ID NO:1), the 410 bp deletion of Glycine max promoter p-47116125 (SEQ ID NO:3), and the 210 bp deletion of Glycine max promoter p-47116125 (SEQ ID NO:3).

FIG. 12: Table showing general sequence formulas (formula 1 and formula 2) of sequence elements identified in minimal promoter polynucleotide fragments.

FIG. 13: General sequence for minimal promoter polynucleotide fragment of A. thaliana promoter region of locus At1g21460 (pWT128) (SEQ ID NO:43) and table showing 16 sequence elements contained in SEQ ID NO. 43.

FIG. 14: General sequence for minimal promoter polynucleotide fragment of A. thaliana promoter region of locus At5g53190 (SEQ ID NO:44) and table showing 9 sequence elements contained in SEQ ID NO. 44

FIG. 15: General sequence for minimal promoter polynucleotide fragment of Glycine max promoter region of the gene corresponding to cDNA clone 47116125 (SEQ ID NO:45) and table showing 7 sequence elements contained in SEQ ID NO. 45

DETAILED DESCRIPTION OF PREFERRED EMBODIMENTS

The present invention may be understood more readily by reference to the following detailed description of the preferred embodiments of the invention and the examples included herein. Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5$^{th}$ Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that this invention is not limited to specific nucleic acids, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook and Russell, 2001 Molecular Cloning, Third Edition, Cold Spring Harbor, Plainview, New York; Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York.

The nucleic acids according to the present invention may be provided isolated and/or purified from their natural environment, in substantially pure or homogeneous form, or free or substantially free of other nucleic acids of the species of origin. An "isolated" nucleic acid as used herein is also substantially free—at the time of its isolation—of other cellular materials or culture medium when produced by recombinant techniques, or substantially free of chemical precursors when chemically synthesized. The promoters of the invention are isolated nucleic acids. Where used herein, the term "isolated" encompasses all of these possibilities.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "promoter" as used herein refers to a DNA sequence which, when ligated to a nucleotide sequence of interest, is capable of controlling the transcription of the nucleotide sequence of interest into mRNA. A promoter is typically, though not necessarily, located 5' (e.g., upstream) of a nucleotide of interest (e.g., proximal to the transcriptional start site of a structural gene) whose transcription into mRNA it controls, and provides a site for specific binding by RNA polymerase and other transcription factors for initiation of transcription. A "constitutive promoter" refers to a promoter that is able to express the open reading frame or the regulatory element that it controls in all or nearly all of the plant tissues during all or nearly all developmental stages of the plant. "Regulated promoter" refers to promoters that direct gene expression not constitutively, but in a temporally- and/or spatially manner, and includes both tissue-specific and inducible promoters. Different promoters may direct the expression of a gene or regulatory element in different tissues or cell types, or at different stages of development, or in response to different environmental conditions. "Tissue-specific promoter" refers to regulated promoters that are not expressed in all plant cells but only in one or more cell types in specific organs (such as roots or seeds), specific tissues (such as embryo or cotyledon), or specific cell types (such as leaf parenchyma or seed storage cells). "Inducible promoter" refers to those regulated promoters that can be turned on in one or more cell types by an external stimulus, such as a chemical, light, hormone, stress, or a pathogen.

In accordance with the invention, the promoter polynucleotides of the present invention may be placed in operative association with a second polynucleotide for root-specific and/or nematode-inducible expression of the second polynucleotide in plants in order to vary the phenotype of that plant. As used herein, the terms "in operative association," "operably linked," and "associated with" are interchangeable and mean the functional linkage of a promoter polynucleotide and a second polynucleotide on a single nucleic acid fragment in such a way that the transcription of the second polynucleotide is initiated and mediated by the promoter polynucleotide. In general, nucleic acids that are in operative association are contiguous.

Second polynucleotide sequences include, for example, an open reading frame, a portion of an open reading frame, a nucleic acid encoding a fusion protein, an anti-sense sequence, a sequence encoding a double-stranded RNA sequence, a transgene, and the like. For example, the second polynucleotide may encode an insect resistance gene, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker gene, a positive selectable marker gene, a gene affecting plant agronomic characteristics (i.e., yield), an environmental stress resistance gene (as exemplified by genes imparting resistance or tolerance to drought, heat, chilling, freezing, excessive moisture, salt stress, or oxidative stress), genes which improve starch properties or quantity, oil quantity and quality, amino acid or protein composition, and the like. In case the promoter of the invention is used in plants of the family Fabaceae to mediate expression in root-nodules, the second nucleic acid can be a gene affecting plant agronomic characteristics such as nitrogen fixation, nitrogen transport, plant protein content or seed protein content and the like.

Preferably, the second polynucleotide encodes a double-stranded RNA (dsRNA) or anti-sense polynucleotide, which is substantially identical or homologous in whole or in part to a plant gene required for formation or maintenance of a nematode feeding site. The second polynucleotide may alternatively encode an agent that disrupts the growth and/or reproduction of plant parasitic nematodes, that confers or improves plant resistance to plant parasitic nematodes, or that is toxic to plant parasitic nematodes to reduce crop destruction. Any polynucleotide encoding an agent that disrupts the growth and/or reproduction of plant parasitic nematodes, that confers or improves plant resistance to plant parasitic nematodes, or that is toxic to plant parasitic nematodes may be employed in accordance with the invention. For example, the second polynucleotide may encode a double-stranded RNA that is substantially identical to a target gene of a parasitic plant nematode that is essential for metabolism, survival, metamorphosis, or reproduction of the nematode. The second polynucleotide may encode a double-stranded RNA that is substantially identical to a plant gene in the feeding sites of the plant roots that is essential for the survival of the nematodes. As used herein, taking into consideration the substitution of uracil for thymine when comparing RNA and DNA sequences, the terms "substantially identical" and "corresponding to" mean that the nucleotide sequence of one strand of the dsRNA is at least about 80%-90% identical to 20 or more contiguous nucleotides of the target gene, more preferably, at least about 90-95% identical to 20 or more contiguous nucleotides of the target gene, and most preferably at least about 95-99% identical or absolutely identical to 20 or more contiguous nucleotides of the target gene. Exemplary plant parasitic nematode target genes are set forth, for example, in commonly assigned co-pending U.S. Patent Application Publication No. 2005/188438, incorporated herein by reference.

Alternatively, for nematode control, the second polynucleotide placed in operative association with the promoters of the invention may encode a nematode-toxic protein. For example, polynucleotides encoding microbial toxins or fragments thereof, toxins or fragments thereof derived from insects such as those described in U.S. Pat. Nos. 5,457,178; 5,695,954; 5,763,568; 5,959,182; and the like, are useful in this embodiment of the invention.

Alternatively, nematodes can be controlled by disrupting or eradicating the feeding sites, syncytia or giant cells, using a method of down-regulating genes essential for development and maintenance of a nematode feeding site, syncytia, or giant cell, by disrupting the function of the present invention promoters using methods known to those of skill in the art such as antisense or RNAi sequences.

Crop plants and corresponding pathogenic nematodes are listed in Index of Plant Diseases in the United States (U.S. Dept. of Agriculture Handbook No. 165, 1960); Distribution of Plant-Parasitic Nematode Species in North America (Society of Nematologists, 1985); and Fungi on Plants and Plant Products in the United States (American Phytopathological Society, 1989). For example, plant parasitic nematodes that are targeted by the present invention include, without limitation, cyst nematodes and root-knot nematodes. Specific plant parasitic nematodes which are targeted by the present invention include, without limitation, *Heterodera glycines, Heterodera schachtii, Heterodera avenae, Heterodera oryzae, Heterodera cajani, Heterodera trifolii, Globodera pallida, G. rostochiensis,* or *Globodera tabacum, Meloidogyne incognita, M. arenaria, M. hapla, M. javanica, M. naasi, M. exigua, Ditylenchus dipsaci, Ditylenchus angustus, Radopholus similis, Radopholus citrophilus, Helicotylenchus multicinctus, Pratylenchus coffeae, Pratylenchus brachyurus, Pratylenchus vulnus, Paratylenchus curvitatus, Paratylenchus zeae, Rotylenchulus reniformis, Paratrichodorus anemones, Paratrichodorus minor, Paratrichodorus christiei, Anguina tritici, Bidera avenae, Subanguina radicicola, Hoplolaimus seinhorsti, Hoplolaimus Columbus, Hoplolaimus galeatus, Tylenchulus semipenetrans, Hemicycliophora arenaria, Rhadinaphelenchus cocophilus, Belonolaimus longicaudatus, Trichodorus primitivus, Nacobbus aberrans, Aphelenchoides besseyi, Hemicriconemoides kanayaensis, Tylenchorhynchus claytoni, Xiphinema americanum, Cacopaurus pestis,* and the like.

In one embodiment, the targeted nematodes belong to nematode families inducing giant or syncytial cells. Nematodes inducing giant or syncytial cells belong to the families Longidoridae, Trichodoridae, Heterodidae, Meloidogynidae, Pratylenchidae or Tylenchulidae. In particular to the families Heterodidae and Meloidogynidae.

Accordingly, in another embodiment the targeted nematodes belong to one or more genus selected from the group of *Naccobus, Cactodera, Dolichodera, Globodera, Heterodera, Punctodera, Longidorus* or *Meloidogyne*. In a preferred embodiment the targeted nematodes belong to one or more genus selected from the group of Naccobus, Cactodera, Dolichodera, Globodera, Heterodera, Punctodera or Meloidogyne. In a more preferred embodiment the targeted nematodes belong to one or more genus selected from the group of Globodera, Heterodera, or Meloidogyne. In an even more preferred embodiment the targeted nematodes belong to one or both genus selected from the group of Globodera or Heterodera. In another embodiment the targeted nematodes belong to the genus *Meloidogyne*.

When the targeted nematodes are of genus *Globodera*, the species targeted may be selected from the group consisting of *G. achilleae, G. artemisiae, G. hypolysi, G. mexicana, G. millefolii, G. mali, G. pallida, G. rostochiensis, G. Tabacum,* and *G. virginiae*. In a preferred embodiment the targeted *Globodera* nematode includes at least one of the species *G. pallida, G. tabacum,* or *G. rostochiensis*. When the targeted nematode is of genus *Heterodera*, the species may be selected from the group consisting of *H. avenae, H. carotae, H. ciceri, H. cruciferae, H. delvii, H. elachista, H. filipjevi, H. gambiensis, H. glycines, H. goettingiana, H. graduni, H. humuli, H. hordecalis, H. latipons, H. major, H. medicaginis, H. oryzicola, H. pakistanensis, H. rosii, H. sacchari, H. schachtii, H. sorghi, H. trifolii, H. urticae, H. vigni* and *H. zeae*. In a preferred embodiment the targeted *Heterodera* nematodes include at least one of the species *H. glycines, H. avenae, H. cajani, H. gottingiana, H. trifolii, H. zeae* or *H. schachtii*. In a more preferred embodiment the targeted nematodes includes at least one of the species *H. glycines* or *H. schachtii*. In a most preferred embodiment the targeted nematode is the species *H. glycines*.

When the targeted nematodes are of the genus *Meloidogyne*, the targeted nematode may be selected from the group consisting of *M. acronea, M. arabica, M. arenaria, M. artiellia, M. brevicauda, M. camelliae, M. chitwoodi, M. cofeicola, M. esigua, M. graminicola, M. hapla, M. incognita, M. indica, M. inornata, M. javanica, M. lini, M. mali, M. microcephala, M. microtyla, M. naasi, M. salasi* and *M. thamesi*. In a preferred embodiment the targeted nematodes includes at least one of the species *M. javanica, M. incognita, M. hapla, M. arenaria* or *M. chitwoodi*.

Any plant species can be transformed with the promoter polynucleotides of the invention. For example, Plants which may be transformed with nucleic acid constructs containing the promoter polynucleotides of the present invention include, without limitation, plants from a genus selected from the group consisting of Medicago, Lycopersicon, Brassica, Cucumis, Solanum, Juglans, Gossypium, Malus, Vitis, Antirrhinum, Populus, Fragaria, Arabidopsis, Picea, Capsicum, Chenopodium, Dendranthema, Pharbitis, Pinus, Pisum, Oryza, Zea, Triticum, Triticale, Secale, Lolium, Hordeum, Glycine, Pseudotsuga, Kalanchoe, Beta, Helianthus, Nicotiana, Cucurbita, Rosa, Fragaria, Lotus, Medicago, Onobrychis, trifolium, Trigonella, Vigna, Citrus, Linum, Geranium, Manihot, Daucus, Raphanus, Sinapis, Atropa, Datura, Hyoscyamus, Nicotiana, Petunia, Digitalis, Majorana, Clahorium, Lactuca, Bromus, Asparagus, Antirrhinum, Heterocallis, Nemesis, Pelargonium, Panicum, Pennisetum, Ranunculus, Senecio, Salpiglossis, Browaalia, Phaseolus, Avena, and Allium.

Derivatives and variants of the promoter polynucleotides can preferably be used in particular plant clades, families, genus or plant species. Derivatives and variants of the promoter polynucleotides which can be isolated from one plant species are preferably used in plants of the same clade, family, genus or species of plants of which the plant, used for isolation of the derivative and variant of the promoter polynucleotides, belongs to. Accordingly in one embodiment the plant is a monocotyledonous plant, preferably a plant of the family Poaceae, Musaceae, Liliaceae or Bromeliaceae, preferably of the family Poaceae. Accordingly, in yet another embodiment the plant is a Poaceae plant of the genus *Zea, Triticum, Oryza,*

*Hordeum, Secale, Avena, Saccharum, Sorghum, Pennisetum, Setaria, Panicum, Eleusine, Miscanthus, Brachypodium, Festuca* or *Lolium*. When the plant is of the genus *Zea*, the preferred species is *Z. mays*. When the plant is of the genus *Triticum*, the preferred species is *T. aestivum*, T. speltae or T. durum. When the plant is of the genus *Oryza*, the preferred species is *O. sativa*. When the plant is of the genus *Hordeum*, the preferred species is *H. vulgare*. When the plant is of the genus *Secale*, the preferred species *S. cereale*. When the plant is of the genus *Avena*, the preferred species is *A. sativa*. When the plant is of the genus *Saccarum*, the preferred species is *S. officinarum*. When the plant is of the genus *Sorghum*, the preferred species is *S. vulgare, S. bicolor* or *S. sudanense*. When the plant is of the genus *Pennisetum*, the preferred species is *P. glaucum*. When the plant is of the genus *Setaria*, the preferred species is *S. italica*. When the plant is of the genus *Panicum*, the preferred species is *P. miliaceum* or *P. virgatum*. When the plant is of the genus *Eleusine*, the preferred species is *E. coracana*. When the plant is of the genus *Miscanthus*, the preferred species is *M. sinensis*. When the plant is of the genus *Brachypodium*, the preferred species is *B. distachyon*. When the plant is a plant of the genus *Festuca*, the preferred species is *F. arundinaria, F. rubra* or *F. pratensis*. When the plant is of the genus *Lolium*, the preferred species is *L. perenne* or *L. multiflorum*. Alternatively, the plant may be Triticosecale.

Alternatively, in one embodiment the plant is a dicotyledonous plant, preferably a plant of the family Fabaceae, Solanaceae, Brassicaceae, Chenopodiaceae, Asteraceae, Malvaceae, Linacea, Euphorbiaceae, Convolvulaceae Rosaceae, Cucurbitaceae, Theaceae, Rubiaceae, Sterculiaceae or Citrus. In one embodiment the plant is a plant of the family Fabaceae, Solanaceae or Brassicaceae. Accordingly, in one embodiment the plant is of the family Fabaceae, preferably of the genus *Glycine, Pisum, Arachis, Cicer, Vicia, Phaseolus, Lupinus, Medicago* or *Lens*. Preferred species of the family Fabaceae are *M. truncatula, M. sativa, G. max, P. sativum, A. hypogea, C. arietinum, V. faba, P. vulgaris, Lupinus albus, Lupinus luteus, Lupinus angustifolius* or *Lens culinaris*. More preferred are the species *G. max* and *A. hypogea, M. sativa*. Most preferred is the species *G. max* When the plant is of the family Solanaceae, the preferred genus is *Solanum, Lycopersicon, Nicotiana* or *Capsicum*. Preferred species of the family Solanaceae are *S. tuberosum, L. esculentum, N. tabaccum* or *C. chinense*. More preferred is *S. tuberosum*. Accordingly, in one embodiment the plant is of the family Brassicaceae, preferably of the genus *Arabidopsis, Brassica* or *Raphanus*. Preferred species of the family Brassicaceae are the species *A. thaliana, B. napus, B. oleracea, B. juncea* or *B. rapa*. More preferred is the species *B. napus*. When the plant is of the family Chenopodiaceae, the preferred genus is Beta and the preferred species is the *B. vulgaris*. When the plant is of the family Asteraceae, the preferred genus is *Helianthus* and the preferred species is *H. annuus*. When the plant is of the family Malvaceae, the preferred genus is *Gossypium* or *Abelmoschus*. When the genus is *Gossypium*, the preferred species is *G. hirsutum* or *G. barbadense* and the most preferred species is *G. hirsutum*. A preferred species of the genus *Abelmoschus* is the species *A. escuentus*. When the plant is of the family Linacea, the preferred genus is *Linum* and the preferred species is *L. usitatissimum*. When the plant is of the family Euphorbiaceae, the preferred genus is *Manihot, Jatropa* or *Rhizinus* and the preferred species are *M. esculenta J. curcas*, or *R. comunis*. When the plant is of the family Convolvulaceae, the preferred genus is *Ipomea* and the preferred species is I. batatas. When the plant is of the family Rosaceae, the preferred genus is *Rosa, Malus, Pyrus, Prunus, Rubus, Ribes, Vaccinium* or *Fragaria* and the preferred species is the hybrid *Fragaria× ananassa*. When the plant is of the family Cucurbitaceae, the preferred genus is *Cucumis, Citrullus* or *Cucurbita* and the preferred species is *Cucumis sativus, Citrullus lanatus*, or *Cucurbita pepo*. When the plant is of the family Theaceae, the preferred genus is *Camellia* and the preferred species is *C. sinensis*. When the plant is of the family Rubiaceae, the preferred genus is *Coffea* and the preferred species is *C. arabica* or *C. canephora*. When the plant is of the family Sterculiaceae, the preferred genus is *Theobroma* and the preferred species is *T. cacao*. When the plant is of the genus *Citrus*, the preferred species is *C. sinensis, C. limon, C. reticulata, C. maxima*, and hybrids of *Citrus* species, or the like.

The *Arabidopsis* promoters polynucleotides of the invention (SEQ ID NO:1 and SEQ ID NO:2) represent promoter regions of *Arabidopsis* homologs of the soybean cDNA clone 47116125 (SEQ ID NO:4) the coding sequence is annotated as *Medicago truncatula* Nodulin 3-like (MtN3-like) gene. The *Arabidopsis* promoter polynucleotides were isolated from Arabidopsis genomic DNA as disclosed in Example 2. The soybean MtN3-like promoter polynucleotide of this invention (SEQ ID NO:3) was isolated from soybean genomic DNA as disclosed in Example 1. As demonstrated in Example 3, when the *Arabidopsis* and soybean promoter polynucleotides of the invention were placed in operative association with a GUS reporter gene, the expression of GUS gene was up-regulated in soybean hairy roots infected by nematodes.

The invention is thus embodied in a promoter comprising an isolated promoter polynucleotide having a sequence as set forth in SEQ ID NO:1, SEQ ID NO:2, or SEQ ID NO:3, or a minimal promoter polynucleotide fragment derived from an isolated promoter polynucleotide having a sequence as set forth in SEQ ID NO:1, SEQ ID NO:2, or SEQ ID NO:3 which is capable of driving root-specific and/or nematode-inducible expression of a second polynucleotide. The methods disclosed herein may be employed to isolate additional minimal promoter polynucleotide fragments of SEQ ID NO:1, SEQ ID NO:2, or SEQ ID NO:3 which are capable of mediating root-specific and/or nematode-inducible expression of a second polynucleotide.

Alternatively, the promoter of the invention comprises an isolated promoter polynucleotide which hybridizes under stringent conditions to a nucleic acid having a sequence as set forth in SEQ ID NO:1, SEQ ID NO:2, or SEQ ID NO:3, or a minimal promoter polynucleotide fragment derived from an isolated promoter polynucleotide having a sequence as set forth in SEQ ID NO:1, SEQ ID NO:2, or SEQ ID NO:3. Stringent hybridization conditions as used herein are well known, including, for example, 400 mM NaCl, 40 mM PIPES pH 6.4, 1 mM EDTA, 60° C. hybridization for 12-16 hours; followed by washing in 0.1% SDS, 0.1% SSC at approximately 650C for about 15-60 minutes. The invention is further embodied in an isolated promoter polynucleotide capable of driving root-specific and/or nematode-inducible expression of a second polynucleotide that hybridizes under stringent conditions to a promoter polynucleotide comprising nucleotides 748 to 998, or 500 to 998, or 573 to 922 of a sequence as set forth in SEQ ID NO:1; a nucleic acid that hybridizes under stringent conditions to a nucleic acid comprising nucleotides 1637 to 1986 of a sequence as set forth in SEQ ID NO:2; a nucleic acid that hybridizes under stringent conditions to a nucleic acid comprising nucleotides 400 to 609, or 260 to 609, or 200 to 609 of a sequence as set forth in SEQ ID NO:3; wherein the promoter polynucleotide is induced in roots of a plant by plant parasitic nematodes.

The promoter of the invention further comprises an isolated promoter polynucleotide capable of driving root-specific and/or nematode-inducible expression of a second polynucleotide which is at least 50-60%, or at least 60-70%, or at least 70-80%, 80-85%, 85-90%, 90-95%, or at least 95%, 96%, 97%, 98%, 99% or more identical or similar to a nucleic acid having a sequence as set forth in SEQ ID NO; 1, 2, or 3, or to a minimal promoter polynucleotide fragment derived from a nucleic acid having a sequence as set forth in SEQ ID NO:1, 2 or 3. The length of the sequence comparison for polynucleotides is at least 50 consecutive nucleotides, or at least 100 consecutive nucleotides, or at least 200 consecutive nucleotides, or at least 500 consecutive nucleotides, up to the whole length of the sequence. In case the two sequences to be compared do not have a identical length, the term "the whole length of the sequence" refers to the whole length of the shorter sequence.

In one embodiment the promoter of the invention comprises an isolated promoter polynucleotide capable of driving root-specific and/or nematode-inducible expression of a second polynucleotide which is at least 70-80%, 80-85%, 85-90%, 90%, 91%, 92%, 93%, 94%, 95%, 95%, 96%, 97%, 98%, 99% or more identical or is identical to a nucleic acid having a sequence as set forth in SEQ ID NO; 43, 44 or 45. In another embodiment the isolated promoter polynucleotide being similar to a sequence as set forth in SEQ ID NO; 43, 44 or 45 is 20, 10, 9, 8, 7, 6, 5, 4, 3, 2, or 1 nucleotides shorter then the sequence as set forth in SEQ ID NO: 43, 44 or 45.

In another embodiment the isolated promoter polynucleotide is at least 70-80%, 80-85%, 85-90%, 90%, 91%, 92%, 93%, 94%, 95%, 95%, 96%, 97%, 98%, 99% or more identical or is identical to a nucleic acid having a sequence as set forth in SEQ ID NO; 43, and is shorter than SEQ ID NO: 43 by 20, 10, 9, 8, 7, 6, 5, 4, 3, 2, 1 nucleotides, or is not shorter than SEQ ID NO: 43. Preferably the isolated promoter polynucleotide does contain at least 10, 11, 12, 13, 14, or all elements as described in FIG. 13 and being positioned at the same polynucleotide strand (− or +strand) as described in the table of FIG. 13. Preferably the elements in FIG. 13 have a sequence as described by SEQ ID NO: 25, 26, 27, 28, 29, 30, 31, 32, 33, 34, 35, 36, 37, 38, 39, 40, 41 or 42 according to FIG. 12, more preferably they have a sequence as described by SEQ ID NO: 34, 35, 36, 37, 38, 39, 40, 41 or 42 according to FIG. 12.

In another embodiment the isolated promoter polynucleotide is at least 70-80%, 80-85%, 85-90%, 90%, 91%, 92%, 93%, 94%, 95%, 95%, 96%, 97%, 98%, 99% or more identical or is identical to a nucleic acid having a sequence as set forth in SEQ ID NO; 44, and is shorter than SEQ ID NO: 44 by 20, 10, 9, 8, 7, 6, 5, 4, 3, 2, 1 nucleotides or is not shorter than SEQ ID NO: 44. Preferably the isolated promoter polynucleotide does contain at least 3, 4, 5, 6, 7, 8 or all elements as described in FIG. 14 and being positioned at the same polynucleotide strand (− or +strand) as described in the table of FIG. 14. Preferably the elements in FIG. 14 have a sequence as described by SEQ ID NO: 25, 26, 27, 28, 30, 32, 33, 34, 35, 36, 37, 39, 41 or 42, according to FIG. 12, more preferably the have a sequence as described by SEQ ID NO: 34, 35, 36, 37, 39, 41 or 42 according to FIG. 12.

In another embodiment the isolated promoter polynucleotide is at least 70-80%, 80-85%, 85-90%, 90%, 91%, 92%, 93%, 94%, 95%, 95%, 96%, 97%, 98%, 99% or more identical or is identical to a nucleic acid having a sequence as set forth in SEQ ID NO; 45, and is shorter than SEQ ID NO: 45 by 20, 10, 9, 8, 7, 6, 5, 4, 3, 2, 1 nucleotides or is not shorter than SEQ ID NO: 45. Preferably the isolated promoter polynucleotide does contain at least 1, 2, 3, 4, 5, 6 or all elements as described in FIG. 15 and being positioned at the same polynucleotide strand (− or +strand) as described in the table of FIG. 15. Preferably the elements in FIG. 15 have a sequence as described by SEQ ID NO: 25, 26, 27, 28, 29, 31, 34, 35, 36, 37, 38 or 40, according to FIG. 12, more preferably the have a sequence as described by SEQ ID NO: 34, 35, 36, 37, 38 or 40 according to FIG. 12.

The term "sequence identity" or "identity" in the context of two nucleic acid or polypeptide sequences makes reference to those positions in the two sequences where identical pairs of symbols fall together when the sequences are aligned for maximum correspondence over a specified comparison window, for example, either the entire sequence as in a global alignment or the region of similarity in a local alignment. When percentage of sequence identity is used in reference to proteins it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those skilled in the art. Typically this involves scoring a conservative substitution as a partial match rather than a mismatch, thereby increasing the percentage of sequence similarity.

As used herein, "percentage of sequence identity" or "sequence identity percentage" denotes a value determined by first noting in two optimally aligned sequences over a comparison window, either globally or locally, at each constituent position as to whether the identical nucleic acid base or amino acid residue occurs in both sequences, denoted a match, or if it does not, denoted a mismatch. As said alignments are constructed by optimizing the number of matching bases, while concurrently allowing both for mismatches at any position and for the introduction of arbitrarily-sized gaps, or null or empty regions where to do so increases the significance or quality of the alignment, the calculation determines the total number of positions for which the match condition exists, and then divides this number by the total number of positions in the window of comparison, and lastly multiplies the result by 100 to yield the percentage of sequence identity. "Percentage of sequence similarity" for protein sequences can be calculated using the same principle, wherein the conservative substitution is calculated as a partial rather than a complete mismatch. Thus, for example, where an identical amino acid is given a score of 1 and a non-conservative substitution is given a score of zero, a conservative substitution is given a score between zero and 1. The scoring of conservative substitutions can be obtained from amino acid matrices known in the art, for example, Blosum or PAM matrices.

Methods of alignment of sequences for comparison are well known in the art. The determination of percent identity or percent similarity (for proteins) between two sequences can be accomplished using a mathematical algorithm. Preferred, non-limiting examples of such mathematical algorithms are, the algorithm of Myers and Miller (Bioinformatics, 4(1):11-17, 1988), the Needleman-Wunsch global alignment (J. Mol. Biol., 48(3):443-53, 1970), the Smith-Waterman local alignment (J. Mol. Biol., 147:195-197, 1981), the search-for-similarity-method of Pearson and Lipman (PNAS, 85(8): 2444-2448, 1988), the algorithm of Karlin and Altschul (Altschul et al., J. Mol. Biol., 215(3):403-410, 1990; PNAS, 90:5873-5877, 1993). Computer implementations of these mathematical algorithms can be utilized for comparison of sequences to determine sequence identity or to identify homologs.

The invention further embodies "variants" or "derivatives" of the promoter polynucleotides of the invention. Derivatives of the specific promoter polynucleotide sequences and their specific elements may include, but are not limited to, deletions of sequence, single or multiple point mutations, alterations at a particular restriction enzyme site, addition of functional elements, or other means of molecular modification. This modification may or may not enhance, or otherwise alter the transcription regulating activity of said promoter polynucleotide.

For example, one of skill in the art may delimit the functional elements e.g. promoter elements such like, but not limited to, transcription factor binding sites within the sequences and delete any non-essential functional elements. Functional elements may be modified or combined to increase the utility or increase the expression level of the promoter polynucleotides of the invention for any particular application.

The term "equivalent fragment" or "minimal promoter polynucleotide fragment" as used herein refers to a fragment of a promoter polynucleotide that is capable of mediating root-specific and/or nematode-inducible expression of a second polynucleotide. Functionally equivalent fragments of a promoter polynucleotide of the invention can also be obtained by removing e.g. by deletion of non-essential functional elements without deleting the essential ones, e.g. transcription factor binding sites. Narrowing the promoter polynucleotide to its essential, functional elements can be realized in vitro by trial-and-error deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the BIOBASE database "Transfac" (Biologische Datenbanken GmbH, Braunschweig; Wingender 2001) or the database PlantCARE (Lescot 2002). Especially preferred are equivalent fragments of promoter polynucleotides, which are obtained by deleting the region encoding the 5'-untranslated region of the mRNA, thus only providing the (untranscribed) promoter polynucleotide region. The 5'-untranslated region can be easily determined by methods known in the art (such as 5'-RACE analysis). Accordingly, some of the promoter polynucleotides of the invention are equivalent fragments of other promoter polynucleotides. Specific minimal promoter polynucleotide fragments of the invention include, without limitation, a polynucleotide comprising nucleotides 748 to 998, or 500 to 998, or 573 to 922 of a sequence as set forth in SEQ ID NO:1, a polynucleotide comprising nucleotides 1637 to 1986 of a sequence as set forth in SEQ ID NO:2, and a polynucleotide comprising nucleotides 400 to 609, or 260 to 609, or 200 to 609 of a sequence as set forth in SEQ ID NO:3, a polynucleotide comprising a fragment of at least 50 consecutive nucleotides, or at least 100 consecutive nucleotides, or at least 200 consecutive nucleotides of a polynucleotide having a sequence as set forth in SEQ ID NO:1, 2, or 3.

As indicated above, deletion mutants of the promoter polynucleotides of the invention can also be randomly prepared and then assayed. With this strategy, a series of constructs are prepared, each containing a different fragment of the promoter polynucleotide. These constructs are then screened for activity. A suitable means for screening for activity is to attach a promoter polynucleotide, which contains a promoter polynucleotide fragment to a selectable or screenable marker, and to isolate only those cells expressing the marker gene. In this way, a number of different, deleted promoter polynucleotide constructs are identified which still retain the desired, or even enhanced, activity. The smallest promoter polynucleotide fragment, which is required for activity, is thereby identified through comparison of the selected constructs. This promoter polynucleotide fragment may then be used for the construction of vectors for the expression of a second polynucleotide e.g. coding for exogenous genes.

The means for mutagenizing or creating deletions in a polynucleotide e.g. a promoter polynucleotide are well known to those of skill in the art and are disclosed, for example, in U.S. Pat. No. 6,583,338, incorporated herein by reference in its entirety. One example of a regulatory sequence variant is a promoter polynucleotide formed by one or more deletions from a larger promoter polynucleotide. The 5' portion of a promoter polynucleotide up to the TATA box near the transcription start site can sometimes be deleted without abolishing promoter polynucleotide activity, as described by Zhu et al., (1995) The Plant Cell 7:1681-1689. A routine way to remove part of a polynucleotide is to use an exonuclease in combination with DNA amplification to produce unidirectional nested deletions of double-stranded DNA clones. A commercial kit for this purpose is sold under the trade name Exo-Size™ (New England Biolabs, Beverly, Mass.). Biologically active variants also include, for example, the native promoter polynucleotides of the invention having one or more nucleotide substitutions, deletions or insertions.

Derivatives and variants also include homologs, paralogs and orthologs from other species, such as but not limited to, bacteria, fungi, and plants. "Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Paralog" refers to a polynucleotide or polypeptide that within the same species which is functionally similar. "Ortholog" refers to a polynucleotide or polypeptide that is the functional equivalent of the polynucleotide or polypeptide in another species. An orthologous gene means preferably a gene, which is encoding an orthologous protein. More specifically, the term "ortholog" denotes a polypeptide or protein obtained from one species that is the functional counterpart of a polypeptide or protein from a different species. Sequence differences among orthologs are the result of speciation.

One of the embodiments encompasses allelic variants of a polynucleotide capable of mediating root-preferred and/or pathogen-inducible expression selected from the group consisting of a) a polynucleotide having a sequence as set forth in SEQ ID NO:1, 2, or 3; b) a polynucleotide comprising nucleotides 748 to 998, or nucleotides 500 to 998, or nucleotides 573 to 922 of a polynucleotide having the sequence as set forth in SEQ ID NO:1; c) a polynucleotide comprising nucleotides 1637 to 1986 of a polynucleotide having the sequence as set forth in SEQ ID NO:2; d) a polynucleotide comprising nucleotides 400 to 609, or nucleotides 260 to 609, or nucleotides 200 to 609 of a polynucleotide having the sequence as set forth in SEQ ID NO:3; e) a polynucleotide having at least 70% sequence identity to any of the polynucleotides of a) through d); f) a polynucleotide hybridizing under stringent conditions to any of the polynucleotides of a) through d); and g) a polynucleotide comprising a fragment of at least 50 consecutive nucleotides, or at least 100 consecutive nucleotides, or at least 200 consecutive nucleotides of a polynucleotide having a sequence as set forth in SEQ ID NO:1, 2, or 3. As used herein, the term "allelic variant" refers to a polynucleotide containing polymorphisms that lead to changes in the nucleotides of the polynucleotide and that exist within a natural population (e.g., a plant species or variety). The term "allelic variant" also refers to a polynucleotide containing polymorphisms that lead to changes in the amino acid sequences of a protein encoded by the nucleotide and that exist within a natural population (e.g. in a plant species or variety). Such natural allelic variations can typically result in 1-5% variance in a polynucleotide, or 1-5% variance in the encoded protein. Allelic variants can be identified by sequencing the polynucleotide of interest in a number of different plants, which can be readily carried out by using, for example, hybridization probes to identify the same promoter polynucleotide, gene or genetic locus in those plants. Any and all such nucleic acid variations in a polynucleotide which are the result of natural allelic variation and do not alter the functional activity of the polynucleotide, and any and all such amino acid polymorphisms or variations of a protein that are the result of natural allelic variation and do not alter the functional activity of the protein, are intended to be within the scope of the invention Allelic variants or orthologs of a gene may be used to clone variants of the promoter polynucleotides of the invention.

Accordingly in one embodiment the promoter polynucleotide of the invention is obtainable from a genomic fragment comprising a promoter polynucleotide being at least 30%, 40%, 50%, 60%, 70%, 80%, 85%, 90%, 95%, 96%, 97%, 98%, 99% or 100% identical to the sequence as described by SEQ ID NO:1, 2, or 3; or a polynucleotide comprising nucleotides 748 to 998, or nucleotides 500 to 998, or nucleotides 573 to 922 of a polynucleotide having the sequence as set forth in SEQ ID NO:1; or a polynucleotide comprising nucleotides 1637 to 1986 of a polynucleotide having the sequence as set forth in SEQ ID NO:2; or a polynucleotide comprising nucleotides 400 to 609, or nucleotides 260 to 609, or nucleotides 200 to 609 of a polynucleotide having the sequence as set forth in SEQ ID NO:3, which is functionally linked to a polynucleotide coding for a polypeptide sequence, which is at least 80% to 85%, 90%, 91%, 92%, 93%, 94%, 95%, 96%, 97%, 98%, 99% identical or is 100% identical to a sequence as described by SEQ ID NO: 5, SEQ ID NO: 6 or SEQ ID NO: 7. In a preferred embodiment, the genomic fragment is a genomic fragment of a plant. Such plant can be any plant, for example but not limiting to a monocotyledonous or a dicotyledonous plant, preferably it is from a dicotyledonous plant, more preferably it is from a plant belonging to the family Brassicacea or Fabacea. In an even more preferred embodiment it is from a plant belonging to the genus *Arabidopsis* or *Glycine*, most preferably it is from *Arabidopsis thaliana* or *Glycine max*. Accordingly, the promoter polynucleotide of the genomic fragment mediates root-specific and/or nematode-inducible expression of the polypeptide sequence, which is at least 80% to 85%, 90%, 91%, 92%, 93%, 94%, 95%, 96%, 97%, 98%, 99% identical or is 100% identical to a sequence as described by SEQ ID NO: 5, SEQ ID NO: 6 or SEQ ID NO: 7. Preferably the polypeptide sequence, which is at least 80% to 85%, 90%, 91%, 92%, 93%, 94%, 95%, 96%, 97%, 98%, 99% identical or is 100% identical to a sequence as described by SEQ ID NO: 5, SEQ ID NO: 6 or SEQ ID NO: 7 is induced in roots of a plant exposed to a nematode stimulus. Preferably the distance between the promoter polynucleotide and the functionally linked polynucleotide coding for a polypeptide sequence, which is at least 80% to 85%, 90%, 91%, 92%, 93%, 94%, 95%, 96%, 97%, 98%, 99% identical or is 100% identical to a sequence as described by SEQ ID NO: 5, SEQ ID NO: 6 or SEQ ID NO: 7 is not longer than 3000 bp, 2000 bp, 1000 bp, more preferably not longer than 900 bp, 800 bp, 700 bp, 600 bp and even more preferably not more than 500 bp, 400 bp, 300 bp, 200 bp, 100 bp, 50 bp or 0 bp.

In another embodiment, the promoter polynucleotide of the invention is induced in roots of a plant exposed to a nematode stimulus. A nematode stimulus can be present, when the plant is infected or is in the process of becoming infected by plant parasitic nematodes. A promoter polynucleotide mediating expression in response to a nematode stimulus is also called a nematode-inducible promoter polynucleotide. The term root-preferred expression in regard to promoters, promoter polynucleotides, isolated nucleic acids or polynucleotides of the invention means expression mainly in root-tissue, in particular in root vascular tissue. Expression mainly in root-tissue means, that the amount of mRNA produced under control of the promoter polynucleotide of the invention is at least 10 times, 50 times, 100 times or 200 times higher in a particular amount of root-tissue when compared to the amount of mRNA produced in the same amount of other tissue, e.g. leave, stem or flower tissue.

The term root-preferred expression in regard to promoters, promoter polynucleotides, isolated nucleic acids or polynucleotides of the invention means expression mainly in root-tissue, in particular in root vascular tissue. Expression mainly in root-tissue means, that the amount of mRNA produced under control of the promoter polynucleotide of the invention is at least 10 times, 50 times, 100 times or 200 times higher in a particular amount of root-tissue when compared to the amount of mRNA produced in the same amount of other tissue, e.g. leave, stem or flower tissue. In case of plants of the family Fabaceae it can also refer to expression in root-nodules. In another embodiment, the promoter is induced in root-nodules of a Fabacea plant, e.g. in root-nodules of *Glycine max*.

The term "nematode resistance" as used herein refers to the ability of a plant to avoid infection by nematodes, to kill nematodes or to hamper, reduce or stop the development, growth or multiplication of nematodes. This might be archieved by an active process, e.g. by producing a substance detrimental to the nematode or, or by a passive process, like having a reduced nutritional value for the nematode or not developing structures induced by the nematode e.g. syncytial or giant cells. The level of nematode resistance of a plant can be determined in various ways, e.g. by counting the nematodes being able to establish parasitism on that plant, or measuring development times of nematodes, proportion of male and female nematodes or the number of nematode eggs produced.

The invention is also embodied in expression cassettes comprising the promoter polynucleotides of the invention. "Expression cassette" in this context is to be understood broadly as comprising all sequences contained in the cassette which may influence transcription of a nucleic acid of interest and, if applicable, translation thereof. In addition to the promoter polynucleotides of the invention, the expression cassette of the invention may further comprise regulatory elements that improve the function of the promoter polynucleotides, genetic elements that allow transcription and/or translation in prokaryotic and/or eukaryotic organisms, and down-stream (in 3'-direction) regulatory elements such as a transcription termination sequence and a polyadenylation sequence. The various components of the expression cassette of the invention are sequentially and operably linked together. Accordingly, an expression cassette of the invention may comprise a promoter comprising an promoter polynucleotide, capable of mediating root-preferred and/or nematode-inducible expression, wherein the promoter polynucleotide is selected from the group of polynucleotides consisting of a) a polynucleotide having a sequence as set forth in SEQ ID NO:1, 2, or 3; b) a polynucleotide comprising nucleotides 748 to 998, or nucleotides 500 to 998, or nucleotides 573 to 922 of a polynucleotide having the sequence as set forth in SEQ ID NO:1; c) a polynucleotide comprising nucleotides 1637 to 1986 of a polynucleotide having the sequence as set forth in SEQ ID NO:2; d) a polynucleotide comprising nucleotides 400 to 609, or nucleotides 260 to 609, or nucleotides 200 to 609 of a polynucleotide having the sequence as set forth in SEQ ID NO:3; e) a polynucleotide having at least 70% sequence identity to any of the polynucleotides of a) through d); f) a polynucleotide hybridizing under stringent conditions to any of the polynucleotides of a) through d); and g) a polynucleotide comprising a fragment of at least 50 consecutive nucleotides, or at least 100 consecutive nucleotides, or at least 200 consecutive nucleotides of a polynucleotide having a sequence as set forth in SEQ ID NO:1, 2, or 3, h) a polynucleotide obtained or obtainable from a genomic fragment, comprising a promoter polynucleotide being at least 30% identical to any of the polynucleotides of a) through d), and comprising a polynucleotide coding for a polypeptide sequence, which is at least 80% identical to a sequence as described by SEQ ID NO: 5, SEQ ID NO: 6 or SEQ ID NO: 7. and which is functionally linked to the promoter polynucleotide being at least 30% identical to any of the polynucleotides of a) through d), or i) a polynucleotide being an equivalent fragment of any polynucleotide of a) through f. In another embodiment, the promoter is induced in roots of a plant infected by plant parasitic nematodes.

Specific genetic elements that may optionally be included in the expression cassette of the invention include, without limitation, origins of replication to allow replication in bacteria, e.g., the OR1 region from pBR322 or the P15A ori; or elements required for *Agrobacterium* TDNA transfer, such as, for example, the left and/or right borders of the T-DNA. Other components of the expression cassette of the invention may include, without limitation, additional regulatory elements such as, for example, enhancers, introns, polylinkers, multiple cloning sites, operators, repressor binding sites, transcription factor binding sites, and the like. Exemplary enhancers include elements from the CaMV 35S promoter, octopine synthase genes (Ellis et al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g. yeast; Ma 1988). Exemplary plant intron sequences include introns from Adh1, bronze1, actin1, actin 2 (WO 00/760067), or the sucrose synthase intron; see: The Maize Handbook, Chapter 116, Freeling and Walbot, Eds., Springer, New York (1994).

Viral leader sequences may also enhance transcription of nucleic acids of interest by the expression cassette of the invention. For example, leader sequences from Tobacco Mosaic Virus (TMV), Maize Chlorotic Mottle Virus (MCMV), and Alfalfa Mosaic Virus (AMV) have been shown to be effective in enhancing expression. Other leaders known in the art include but are not limited to: Picornavirus leaders, for example, (Encephalomyocarditis virus (EMCV) leader; Potyvirus leaders, Tobacco Etch Virus (TEV) leader; MDMV leader (Maize Dwarf Mosaic Virus); Human immunoglobulin heavy-chain binding protein (BiP) leader, Untranslated leader from the coat protein mRNA of alfalfa mosaic virus (AMV RNA 4).

The expression cassette of the invention also comprises a transcription termination element or polyadenylation signal. Exemplary transcription termination elements include those from the nopaline synthase gene of *Agrobacterium tumefaciens* (Bevan 1983), the terminator for the T7 transcript from the octopine synthase gene of *Agrobacterium tumefaciens*, and the 3' end of the protease inhibitor I or II genes from potato or tomato.

A second polynucleotide to be transcribed into RNA, and, optionally, expressed as a protein is inserted into the expression cassette of the invention for transformation into an organism. In accordance with the invention, the second polynucleotide is placed downstream (i.e., in 3'-direction) of the promoter polynucleotide of the invention and upstream of the transcription termination elements, in covalent linkage therewith. Preferably, the distance between the second nucleic acid sequence and the promoter polynucleotide of the invention is not more than 200 base pairs, more preferably not more than 100 base pairs, most preferably no more than 50 base pairs.

An expression cassette of the invention may also be assembled by inserting a promoter polynucleotide of the invention into the plant genome. Such insertion will result in an operable linkage to a nucleic acid sequence of interest native to the genome. Such insertions allow the nucleic acid of interest to be expressed or over-expressed preferentially in root tissue, after induction by nematodes, as the result of the transcription regulating properties of the promoter polynucleotide of the invention. The insertion may be directed or by chance. Preferably, the insertion is directed and realized, for example, by homologous recombination. By this procedure a natural promoter may be replaced in total or in part by the promoter polynucleotide of the invention, thereby modifying the expression profile of an endogenous gene.

The expression cassette of the invention may be inserted into a recombinant vector, plasmid, cosmid, YAC (yeast artificial chromosome), BAC (bacterial artificial chromosome), or any other vector suitable for transformation into a host cell. Preferred host cells are bacterial cells, in particular bacterial cells used for cloning or storing of polynucleotides or used for trans-formation of plant cells, such like, but not limited to, *Escherichia coli, Agrobacterium tumefaciens* and *Agrobacterium rhizogenes* cells, and plant cells. When the host cell is a plant cell, the expression cassette or vector may become inserted into the genome of the transformed plant cell. Alternatively, the expression cassette or vector may be maintained extra chromosomally. The expression cassette or vector of the invention may be present in the nucleus, chloroplast, mitochondria, and/or plastid of the cells of the plant. Preferably, the expression cassette or vector of the invention is inserted into the chromosomal DNA of the plant cell nucleus.

The expression cassette of the invention may be transformed into a plant to provide a transgenic plant comprising one or more polynucleotides in operative association with a promoter polynucleotide of the invention. The expression cassette may comprise any promoter nucleotide of the invention and may comprise or may comprise not a second polynucleotide. In one embodiment the transgenic plant comprises a promoter comprising a promoter polynucleotide as set forth in SEQ ID NO:1, SEQ ID NO:2, or SEQ ID NO:3, a minimal promoter polynucleotide fragment of SEQ ID NO:1, a minimal promoter polynucleotide fragment of SEQ ID NO:2, or a minimal promoter polynucleotide fragment of SEQ ID NO:3. Alternatively, the trans-genic plant of the invention comprises a promoter polynucleotide capable of mediating root-preferred and/or nematode-inducible expression that hybridizes under stringent conditions to a promoter polynucleotide having a sequence as set forth in SEQ ID NO:1, SEQ ID NO:2, SEQ ID NO:3, a minimal promoter polynucleotide fragment of SEQ ID NO:1, a minimal promoter polynucleotide fragment of SEQ ID NO:2, or a minimal promoter polynucleotide fragment of SEQ ID NO:3. Further, the transgenic plant of the invention comprises a promoter polynucleotide capable of mediating root-preferred and/or nematode-inducible expression having at least 70% sequence identity to a polynucleotide having a sequence as set forth in SEQ ID NO:1, SEQ ID NO:2, SEQ ID NO:3, a minimal promoter fragment of SEQ ID NO:1, a minimal promoter fragment of SEQ ID NO:2, or a minimal promoter fragment of SEQ ID NO:3.

The transgenic plants of the invention are made using transformation methods known to those of skill in the art of plant biotechnology. Any method may be used to transform the recombinant expression vector into plant cells to yield the transgenic plants of the invention. Suitable methods for transforming or transfecting host cells including plant cells can be found, for example, in WO2006/024509 (PCT/EP2005/009366; U.S. Ser. No. 60/606,0789) and in Sambrook et al. supra, and in other laboratory manuals such as Methods in Molecular Biology, 1995, Vol. 44, *Agrobacterium* protocols, Ed: Gartland and Davey, Humana Press, Totowa, N.J.

General methods for transforming dicotyledenous plants are also disclosed, for example, in U.S. Pat. Nos. 4,940,838; 5,464,763, and the like. Methods for transforming specific dicotyledenous plants, for example, cotton, are set forth in U.S. Pat. Nos. 5,004,863; 5,159,135; and 5,846,797. Soybean transformation methods are set forth in U.S. Pat. Nos. 4,992,375; 5,416,011; 5,569,834; 5,824,877; 6,384,301 and in EP 0301749B1. Other plant transformation methods are disclosed, for example, in U.S. Pat. Nos. 4,945,050; 5,188,958; 5,596,131; 5,981,840, and the like.

The term "plant" as used herein can, depending on context, be understood to refer to whole plants, plant cells, plant organs, harvested seeds, and progeny of same. The word "plant" also refers to any plant, particularly, to seed plants, and may include, but not limited to, crop plants. Plant parts include, but are not limited to, stems, roots, shoots, fruits, ovules, stamens, leaves, embryos, meristematic regions, callus tissue, gametophytes, sporophytes, pollen, microspores, hypocotyls, cotyledons, anthers, sepals, petals, pollen, non-harvested seeds and the like. The term "harvested seeds" refers to seeds, which are removed from the plant producing the seeds, while the term "non-harvested seeds" refers to seeds still connected to the plant producing the seeds e.g. being in the state of growing or ripening. The plant may be a monocot or a dicot. The plant can be from a genus selected from the group consisting of maize, wheat, barley, sorghum, rye, triticale, rice, sugarcane, citrus trees, pineapple, coconut, banana, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, *Lotus* sp., *Medicago truncatula*, prerennial grass, ryegrass, and *Arabidopsis thaliana*. In another embodiment the plant is from a genus selected from the group consisting of citrus trees, pineapple, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, *Lotus* sp., *Medicago truncatula* and *Arabidopsis thaliana*. In another embodiment the plant is from a genus selected from the group consisting of citrus trees, pineapple, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, *Lotus* sp., *Medicago truncatula* and *Arabidopsis thaliana*. In another embodiment the plant is from a genus selected from the group consisting of, tobacco, sunflower, pea, alfalfa, soybean, tomato, potato, cotton, tobacco, eggplant, pepper, oilseed rape, canola, beet, cabbage, cauliflower, broccoli, lettuce, *Lotus* sp., *Medicago truncatula* and *Arabidopsis thaliana*. In another embodiment the plant is from a genus selected from the group consisting of maize, wheat, barley, sorghum, rye, triticale, rice, sugarcane, pineapple, coconut, banana, perennial grass and ryegrass.

The transgenic plants of the invention may be crossed with similar transgenic plants or with transgenic plants lacking the promoter polynucleotides of the invention or the promoter polynucleotide of the invention and the second polynucleotide or with non-transgenic plants, using known methods of plant breeding, to prepare seed. Further, the transgenic plant of the present invention may comprise, and/or be crossed to another transgenic plant that comprises, one or more different genes of interest operably linked to a promoter polynucleotide of the present invention or to another promoter, thus creating a "stack" of transgenes in the plant and/or its progeny. The seed is then planted to obtain a crossed fertile transgenic plant comprising the nucleic acid of interest and the promoter polynucleotides of the invention. The crossed fertile transgenic plant may have the particular expression cassette inherited through a female parent or through a male parent. The second plant may be an inbred plant. The crossed fertile trans-genic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the DNA construct.

"Gene stacking" can also be accomplished by transferring two or more genes into the cell nucleus by plant transformation. Multiple genes may be introduced into the cell nucleus during transformation either sequentially or in unison. Multiple genes in plants or target pathogen species can be down-regulated by gene silencing mechanisms, specifically RNAi, by using a single transgene targeting multiple linked partial sequences of interest. Stacked, multiple genes under the control of individual promoters can also be over-expressed to attain a desired single or multiple phenotype. Constructs containing gene stacks of both over-expressed genes and silenced targets can also be introduced into plants yielding single or multiple agronomically important phenotypes. In certain embodiments the nucleic acid sequences of the present invention can be stacked with any combination of polynucleotide sequences of interest to create desired phenotypes. The combinations can produce plants with a variety of trait combinations including but not limited to disease resistance, herbicide tolerance, yield enhancement, cold and drought tolerance. These stacked combinations can be created by any method including but not limited to cross breeding plants by conventional methods or by genetic transformation. If the traits are stacked by genetic transformation, the polynucleotide sequences of interest can be combined sequentially or simultaneously in any order. For example if two genes are to be introduced, the two sequences can be contained in separate transformation cassettes or on the same transformation cassette. The expression of the sequences can be driven by the same or different promoters.

The invention further comprises a crop comprising a plurality of the transgenic plants of the invention, planted together in an agricultural field.

The transgenic plants of the invention may be used in a method of controlling a plant parasitic nematode infestation in a crop, which comprises the step of growing said crop from seeds comprising an expression cassette comprising a plant promoter polynucletotide of the invention in operative association with a second polynucleotide that encodes an agent that disrupts the metabolism, growth and/or reproduction of said plant parasitic nematode, that improves plant tolerance to said plant parasitic nematode, or that is toxic to said plant parasitic nematode, wherein the expression cassette is stably integrated into the genomes plant cells, plants and/or of the seeds. Such agents include, without limitation, a double-stranded RNA which is substantially identical to a target gene of a parasitic plant nematode which is essential for survival, metamorphosis, or reproduction of the nematode; a double-stranded RNA which is substantially identical to a plant gene required to maintain a nematode feeding site; an anti-sense RNA, an siRNA, an miRNA or its precursor, a protein that interferes with the metabolism, survival, metamorphosis or reproduction of the nematode, a microbial toxin, a toxin derived from an insect, that interferes with the metabolism, survival, metamorphosis or reproduction of the nematode, and the like.

The promoter of the present invention comprises an isolated nucleic acid selected from the group consisting of: a) a polynucleotide having a sequence as set forth in SEQ ID NO:1, 2, or 3; b) a polynucleotide comprising nucleotides 748 to 998, or nucleotides 500 to 998, or nucleotides 573 to 922 of a polynucleotide having the sequence as set forth in SEQ ID NO:1; c) a polynucleotide comprising nucleotides 651 to 1000 of a polynucleotide having the sequence as set forth in SEQ ID NO:2; d) a polynucleotide comprising nucleotides 400 to 609, or nucleotides 260 to 609, or nucleotides 200 to 609 of a polynucleotide having the sequence as set forth in SEQ ID NO:3; e) a polynucleotide having at least 70% sequence identity to any of the polynucleotides of a) through d); f a polynucleotide hybridizing under stringent conditions to any of the polynucleotides of a) through d); g) a polynucleotide comprising a biologically active portion of any of the polynucleotides of a) through d); and g) a polynucleotide comprising a fragment of at least 50 consecutive nucleotides, or at least 100 consecutive nucleotides, or at least 200 consecutive nucleotides of a polynucleotide having a sequence as set forth in SEQ ID NO:1, 2, or 3 wherein the promoter is capable of mediating root-specific and/or nematode-inducible expression. In a further embodiment, said nucleic acid comprises nucleotides 748 to 998, or nucleotides 500 to 998, or nucleotides 573 to 922 of a polynucleotide having the sequence as set forth in SEQ ID NO: 1. In a further embodiment, said nucleic acid has at least 70% sequence identity to a polynucleotide selected from the group consisting of a polynucleotide having the sequence as set forth in SEQ ID NO:1, a polynucleotide comprising nucleotides 748 to 998 of SEQ ID NO:1, a polynucleotide comprising nucleotides 500 to 998 of SEQ ID NO:1, and a polynucleotide comprising nucleotides 573 to 922 of SEQ ID NO:1. In a further embodiment, said the nucleic acid comprises nucleotides 651 to 1000 of a polynucleotide having the sequence as set forth in SEQ ID NO:2. In a further embodiment, said the nucleic acid has at least 70% sequence identity to a polynucleotide selected from the group consisting of a polynucleotide having the sequence as set forth in SEQ ID NO:2 and a polynucleotide comprising nucleotides 651 to 1000 of SEQ ID NO:2. In a further embodiment, said the nucleic acid comprises nucleotides 400 to 609, or nucleotides 260 to 609, or nucleotides 200 to 609 of a polynucleotide having the sequence as set forth in SEQ ID NO:3. In a further embodiment, said the nucleic acid has at least 70% sequence identity to a polynucleotide selected from the group consisting of a polynucleotide having the sequence as set forth in SEQ ID NO:3, a polynucleotide comprising nucleotides 400 to 609 of SEQ ID NO:3, a polynucleotide comprising nucleotides 260 to 609 of SEQ ID NO:3, and a polynucleotide comprising nucleotides 200 to 609 of SEQ ID NO:3.

Further, the invention relates to an expression cassette comprising the promoter of the invention, which further comprises one or more operably linked polynucleotides. In a further embodiment said expression cassette is an expression cassette, wherein said operably linked polynucleotide encodes an agent that disrupts metabolism, growth, and/or reproduction of a plant parasitic nematode, that confers or improves plant resistance to a plant parasitic nematode, or that is toxic to a plant parasitic nematode.

Further, the invention relates to a transgenic plant transformed with an expression cassette, wherein the expression cassette comprises an isolated nucleic acid selected from the group consisting of: a) a polynucleotide having a sequence as set forth in SEQ ID NO:1, 2, or 3; b) a polynucleotide comprising nucleotides 748 to 998, or nucleotides 500 to 998, or nucleotides 573 to 922 of a polynucleotide having the sequence as set forth in SEQ ID NO:1; c) a polynucleotide comprising nucleotides 651 to 1000 of a polynucleotide having the sequence as set forth in SEQ ID NO:2; d) a polynucleotide comprising nucleotides 400 to 609, or nucleotides 260 to 609, or nucleotides 200 to 609 of a polynucleotide having the sequence as set forth in SEQ ID NO:3; e) a polynucleotide having at least 70% sequence identity to any of the polynucleotides of a) through d); f) a polynucleotide hybridizing under stringent conditions to any of the polynucleotides of a) through d); g) a polynucleotide comprising a biologically active portion of any of the polynucleotides of a) through d); and h) a polynucleotide comprising a fragment of at least 50 consecutive nucleotides, or at least 100 consecutive nucleotides, or at least 200 consecutive nucleotides of a polynucleotide having a sequence as set forth in SEQ ID NO:1, 2, or 3. In a further embodiment said transgenic plant comprises an expression cassette comprising one or more polynucleotides operably linked to the nucleic acid. In a further embodiment said transgenic plant is selected from the group consisting of maize, wheat, barley, sorghum, rye, triticale, rice, sugarcane, citrus trees, pineapple, coconut, banana, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, *Lotus* sp., *Medicago truncatula*, prerennial grass, ryegrass, and *Arabidopsis thaliana*. In a further embodiment said transgenic plant is transformed with an expression cassette, wherein the expression cassette comprises nucleotides 748 to 998, or nucleotides 500 to 998, or nucleotides 573 to 922 of a polynucleotide having the sequence as set forth in SEQ ID NO:1. In a further embodiment said trans-genic plant is transformed with an expression cassette, wherein the expression cassette comprises a nucleic acid having at least 70% sequence identity to a polynucleotide selected from the group consisting of a polynucleotide having the sequence as set forth in SEQ ID NO:1, a polynucleotide comprising nucleotides 748 to 998 of SEQ ID NO:1, a polynucleotide comprising nucleotides 500 to 998 of SEQ ID NO:1, and a polynucleotide comprising nucleotides 573 to 922 of SEQ ID NO:1. In a further embodiment said transgenic plant is transformed with an expression cassette, wherein the expression cassette comprises a nucleic acid comprising nucleotides 651 to 1000 of a polynucleotide having the sequence as set forth in SEQ ID NO:2. In a further embodiment said transgenic plant is transformed with an expression cassette, wherein the expression cassette comprises a nucleic acid having at least 70% sequence identity to a polynucleotide selected from the group consisting of a polynucleotide having the sequence as set forth in SEQ ID NO:2 and a polynucleotide comprising nucleotides 651 to 1000 of SEQ ID NO:2. In a further embodiment said transgenic plant is transformed with an expression cassette, wherein the expression cassette comprises a nucleic acid comprising nucleotides 400 to 609, or nucleotides 260 to 609, or nucleotides 200 to 609 of a polynucleotide having the sequence as set forth in SEQ ID NO:3. In a further embodiment said transgenic plant is transformed with an expression cassette, wherein the expression cassette comprises a nucleic acid having at lest 70% sequence identity to a polynucleotide selected from the group consisting of a polynucleotide having the sequence as set forth in SEQ ID NO:3, a polynucleotide comprising nucleotides 400 to 609 of SEQ ID NO:3, a polynucleotide comprising nucleotides 260 to 609 of SEQ ID NO:3, and a polynucleotide comprising nucleotides 200 to 609 of SEQ ID NO:3.

Further the invention relates to a method of conferring or improving nematode resistance in a plant, comprising a) preparing a construct comprising the promoter of claim 1 operably linked to one or more polynucleotides, b) transforming a plant cell with the construct of a) wherein the promoter induces transcription of the operably linked polynucleotide in the plant cell in response to a nematode stimulus; and c) regenerating the transformed plant cell to produce a transgenic plant having nematode resistance or improved nematode resistance. In a further embodiment said method is a method, wherein the operably linked nucleic acid encodes an agent that disrupts metabolism, growth, and/or reproduction of a plant parasitic nematode, that confers or improves plant resistance to a plant parasitic nematode, or that is toxic to a plant parasitic nematode. In a further embodiment said method is a method, wherein the promoter is a root-preferred and/or nematode-inducible promoter.

Further the invention relates to a method of conferring or improving nematode resistance in a plant, comprising a) preparing a construct comprising a first nucleic acid that is in antisense complementation to a second nucleic acid sequence having the nucleic acid sequence of claim 1, b) transforming a plant cell with the construct of a) wherein the first nucleotide sequence disrupts or down regulates the regulatory function of the second nucleic acid sequence; and c) regenerating the transformed plant cell to produce a transgenic plant having nematode resistance or improved nematode resistance. In a further embodiment said method is a method, wherein the promoter is a root-preferred or nematode-inducible promoter.

The following examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1

Cloning of MtN3-Like Gene Promoter from Soybean Laser Excision of Syncytia

*Glycine max* cv. Williams 82 was germinated on agar plates for three days and then transferred to germination pouches. One day later, each seedling was inoculated with second stage juveniles (J2) of *H. glycines* race 3. Six days after inoculation, new root tissue was sliced into 1 cm long pieces, fixed, embedded in a cryomold, and sectioned using known methods. Syncytia cells were identified by their unique morphology of enlarged cell size, thickened cell wall, and dense cytoplasm and dissected into RNA extraction buffer using a PALM microscope (P.A.L.M. Microlaser Technologies GmbH, Bernried, Germany).

Total cellular RNA was extracted, amplified, and fluorescently labeled using known methods. As controls, total RNA was isolated from both "non-syncytia" and untreated control roots subjected to the same RNA amplification process. The amplified RNA was hybridized to proprietary soybean cDNA arrays. Table 1 summarizes the expression data as measured by cDNA microarray analysis for this gene across all three cell/tissue samples: Syncytia, SCN infected non-syncytia, and untreated control root tissues. Relative levels of gene expression are shown as normalized signal intensities (±standard deviation). As demonstrated in Table 1, Soybean cDNA clone 47116125 was identified as being up-regulated in syncytia of SCN-infected soybean roots.

TABLE 1

Expression of *Medicago truncatula* Nodulin 3-like (MtN3-like) gene

| Gene Name | Syncytia #1(N) | Syncytia #2(N) | Non-Syncytia | Control Roots |
|---|---|---|---|---|
| 47116125 | 3104 ± 477(4) | 2117 ± 450(5) | 99 ± 62 | 191 ± 90 |

(N)Number of cDNA microarray measurements

As demonstrated in Table 1, Soybean cDNA clone 47116125 was identified as being up-regulated in syncytia of SCN-infected soybean roots. FIG. 4 depicts the sequence of soybean cDNA clone 47116125. The 47116125 cDNA sequence (SEQ ID NO:4) was determined to contain the entire open reading frame sequence based on amino acid homology with Arabidopsis amino acid sequences of locus identifiers At1g21460 and At5g53190 as shown in FIG. 5. The open reading frame of 47116125 cDNA sequence (SEQ ID NO:4) from bases 23 to 787 as shown in FIG. 4 was translated and is represented by SEQ ID NO:5 and the sequence marked 47116125 in FIG. 5.

To clone the promoter sequence of 47116125, the Universal Genome Walking Kit (Clontech Laboratories Inc., Palo Alto, Calif.) was used according to the manufacturer's instructions. For this, soybean (*Glycine max*, Resnik) genomic DNA was extracted using the Qiagen DNAeasy Plant Minikit (Qiagen). The procedure consisted of two PCR amplifications, using an adapter primer and a gene-specific primer for each amplification reaction. The sequences of primers used to isolate the promoters of the invention are shown in FIG. 11. The gene specific primers which target 47116125 (SEQ ID NO:4) were primary primer, 47116125GW (SEQ ID NO:15) and nested primer, 47116125GWnest (SEQ ID NO:16). The adaptor primers used were AP1 (SEQ ID NO:13) and AP2 (SEQ ID NO:14). Using this protocol, several clones were isolated and sequenced.

The longest cloned product was identified as pAW127 (SEQ ID NO:8). A sequence alignment of pAW127 with 47116125 cDNA sequence (SEQ ID NO:4) indicated that this clone is nearly identical to 47116125 as shown in FIG. 7. The sequence mismatches between pAW127 sequence and 47116125 cDNA sequence are marked with an asterisk in FIG. 7. The alignment revealed that pAW127 contained a 609 bp promoter sequence upstream of the ATG from nucleotide 51 to 659 of pAW127 sequence (see FIG. 7). This alignment also revealed a stop codon beginning at bp 627 upstream of the ATG start codon in the same frame, indicating that the start codon beginning at bp 660 is the first start codon of the open reading frame of 47116125 gene sequence. This promoter region was cloned out of pAW127 using standard PCR techniques and the primers 47116125prF (SEQ ID NO:17) and 47116125prR (SEQ ID NO:18). 47116125prF and 47116125prR amplified the 609 bp promoter fragment from pAW127 containing the enzyme restriction sites PstI and AscI respectively for ease of directional cloning. The 47116125 promoter and the 5'UTR sequences, without the restriction sites used for cloning, is shown as SEQ ID NO:3. Nucleotide sequence 1-609 represents the entire promoter sequence with the core promoter region spanning nucleotides 260-609. The putative TATA signal spans nucleotide 513 to 519 and the putative 5' untranslated leader sequence of the mRNA from nucleotides 553-609.

Example 2

Cloning of MtN3-like Gene Promoter Polynucleotides from *Arabidopsis*

The promoter polynucleotide regions of *Arabidopsis* At1g21460 and At5g53190 genes were selected based on the similarity of their encoded amino acid sequences (SEQ ID NO:6 and SEQ ID NO:7, respectively) to the amino acid sequence of soybean cDNA clone 47116125 (SEQ ID NO:5) as shown in FIG. 5. *Arabidopsis* (Columbia cotype) genomic DNA was extracted using the Qiagen DNAeasy Plant Minikit (Qiagen, Valencia, Calif., US). The 998 bp (SEQ ID NO:1) and 1,986 bp (SEQ ID NO:2) genomic DNA regions (promoter polynucleotides) directly upstream of the ATG codon including 5'-untranslated region corresponding to *Arabidopsis* MtN3-like genes with locus identifiers, At1g21460 and At5g53190, respectively, were cloned using standard PCR amplification protocols. The primers used for PCR amplification of the *Arabidopsis* promoter polynucleotide are shown in FIG. 11 and were designed based on the *Arabidopsis* genomic sequence database (TAIR). The primer sequences described by SEQ ID NO:9 contains the PstI restriction site for ease of cloning. The primer sequence described by SEQ ID NO:11 contains the PacI restriction site for ease of cloning. The primer sequences described by SEQ ID NO:10 and SEQ ID NO:12 contain the AscI site for ease of cloning. Primer sequences described by SEQ ID NO:9 and SEQ ID NO:10 were used to amplify the promoter polynucleotide of *Arabidopsis* locus At1g21460 described by SEQ ID NO:1. Primer sequences described by SEQ ID NO:11 and SEQ ID NO:12 were used to amplify the promoter polynucleotide of *Arabidopsis* locus At5g53190 described by SEQ ID NO:2, respectively.

The amplified DNA fragment size for each PCR product was verified by standard agarose gel electrophoresis and the DNA extracted. Purified fragments were cloned into pCR2.1 using the TOPO TA cloning kit following the manufacturer's instructions (Invitrogen) and sequenced using an Applied Biosystem 373A (Applied Biosystems, Foster City, Calif., US) automated sequencer. The 998 bp and 1,986 bp DNA fragments corresponding to the promoter polynucleotides of At1g21460 and At5g53190 are shown as SEQ ID NO:1 and SEQ ID NO:2. The restriction sites introduced in the primers for facilitating cloning are not included in the sequences.

Example 3

Binary Vector Construction for Transformation and Generation of Transgenic Hairy Roots To evaluate the expression activity of the cloned promoter polynucleotide, gene fragments corresponding to nucleotides 1 to 998 of SEQ ID NO:1, nucleotides 1 to 1,986 of SEQ ID NO:2, and nucleotides 1 to 609 of SEQ ID NO:3 were cloned upstream of a GUS reporter gene (bacterial 1-glucuronidase or GUS gene (Jefferson (1987) EMBO J. 6, 3901-3907) to create the binary vectors pWT128qcz, RCB1022 and pAW222qcz, respectively. The plant selectable marker in the binary vectors pWT128qcz and pAW222qcz is a herbicide-resistant form of the acetohydroxy acid synthase (AHAS) gene from *Arabidopsis thaliana* (Sathasivan et al., Plant Phys. 97:1044-50, 1991). ARSENAL (imazapyr, BASF Corp, Florham Park, N.J.) was used as the selection agent. The plant selectable marker in the binary vector RCB1022 is a herbicide-resistant form of the acetohydroxy acid synthase (AHAS) gene from *Arabidopsis thaliana* driven by the constitutive parsley ubiquitin promoter (Sathasivan et al., Plant Phys. 97:1044-50, 1991; Plesch, G.; Ebneth, M. Method for the stable expression of nucleic acids in transgenic plants, controlled by a parsley ubiquitin promoter. Patent Application WO 03/102198 A1; 2003).

In the present example, binary vectors pWT128, and pAW222qcz were transformed into *A. rhizogenes* K599 strain by electroporation. Prior to *A. rhizogenes* inoculation, seeds from *G. max* Williams 82 (SCN-susceptible) were germinated, cotyledons were excised, and the adaxial side was wounded several times. An *A. rhizogenes* suspension was inoculated onto the wounded surface, and the inoculated cotyledon was incubated with the adaxial side up for three days at 25° C. under 16 hour/day lighting. The cotyledons were then transferred onto MS plates containing carbenicillin (to suppress *A. rhizogenes* growth) and 1 µM ARSENAL (imazapyr, BASF Corporation, Florham Park, N.J.) as the selection agent. Hairy roots were induced from the wounding site after two weeks. The roots resistant to ARSENAL and growing on the selection media were harvested and transferred onto fresh selection media of the same composition and incubated at 25° C. in darkness. Two weeks after harvesting hairy roots and culturing them on selection media, the hairy roots were subcultured onto MS media containing carbenicillin but not ARSENAL.

Several independent transgenic hairy root lines were generated from transformation with pAW280. Approximately three weeks after subculturing, the transgenic hairy-root lines were inoculated with *H. glycines* race 3 J2. Twelve days after *H. glycines* inoculation (DAI), the hairy roots were harvested and assayed for β-glucuronidase activity of the GUS gene using 5-bromo-4-chloro-3-indoyl-β-D-glucuronic acid (x-Gluc). At each time point after inoculation, a non-inoculated control plate from each line was also stained in GUS staining solution. The roots were then observed under a microscope for detection of GUS expression. For each transgenic line, 10 randomly picked syncytia were observed and scored for intensity of GUS expression.

The following scoring index was used: "−" for no staining, "+" for weak staining, "++" for strong staining. A round-up average of the 10 counts was used to determine the GUS expression level in the syncytia for that line. In addition, GUS expression level in the same lines for other root tissues such as callus, root-tip, vasculature, cortical and primordial were also recorded using the same GUS scoring index of "−" for no staining, "−/+" indicates that there were approximately 25% of the lines tested showing vascular GUS staining in less than 25% of the root tissue observed, "+" for weak staining, "++" for strong staining. The results for lines transformed with pWT128 and pAW222qcz are presented in FIG. 8.

The result of the GUS staining indicates that for most lines tested, the promoter polynucleotide fragment in pWT128 showed intermediate to strong GUS expression in the syncytia and root vascular tissue at 12 DAI. In contrast, GUS expression in other root parts such as root tips and root cortex was undetected or very weak. In addition, the result of the GUS staining indicates that for most lines tested, the promoter polynucleotide fragment in pAW222qcz showed strong GUS expression in the syncytia and root vascular tissue at 12 DAI. In contrast, GUS expression in other root parts such as root tips and root cortex was undetected or very weak.

Example 4

Cloning Deletions of At1g21460 (SEQ ID NO:1) and p-47116125 (SEQ ID NO:3) Promoter Polynucleotides In order to more accurately define the promoter polynucleotide region of At1g21460 (SEQ ID NO:1) and p-47116125 (SEQ ID NO:3), shorter fragments of the upstream sequence were tested. Plasmid DNA of pWT128 and pAW222qcz was extracted from *E. coli* using the Qiagen Plasmid miniprep kit (Qiagen). The 499 bp and 251 bp promoter polynucleotide deletion fragments of *A. thaliana* locus At1g21460 promoter polynucleotide (SEQ ID NO:1) contained in pWT128 and the 410 bp and 210 bp promoter polynucleotide deletion fragments of *Glycine max* cDNA clone p-47116125 (SEQ ID NO:3) contained in pAW222qcz were amplified using standard PCR amplification protocol. For this, approximately 0.1 μg of pWT128 or pAW222qcz plasmid DNA was used as the DNA template in the PCR reaction. The primers used for PCR amplification of the *Arabidopsis* promoter polynucleotides are shown in FIG. 11 and were designed based on the promoter polynucleotide sequence of *A. thaliana* locus At1g21460 promoter polynucleotide (SEQ ID NO:1) contained in pWT128 or the promoter polynucleotide of *Glycine max* p-47116125 (SEQ ID NO:3) contained in pAW222qcz. The primer sequences described by SEQ ID NO:19, SEQ ID NO:20, SEQ ID NO:22, and SEQ ID NO:23 contain the PstI restriction site for ease of cloning. The primer sequence described by SEQ ID NO:21 anneals to the 3' end of the At1g21460 promoter polynucleotide and AscI site in pWT128 such that the AscI site will be contained in the amplified fragment for ease of cloning. The primer sequence described by SEQ ID NO:24 anneals to the 3' end of the p-47116125 promoter polynucleotide upstream of the AscI site in pAW222qcz such that an AatII site will be contained in the amplified fragment for ease of cloning. Primer sequences described by SEQ ID NO:19 and SEQ ID NO:21 were used to amplify the 499 bp promoter polynucleotide deletion region of *Arabidopsis* locus At1g21460 promoter polynucleotide contained in pWT128. Primer sequences described by SEQ ID NO:20 and SEQ ID NO:21 were used to amplify the 251 bp promoter polynucleotide deletion region of *Arabidopsis* locus At1g21460 promoter polynucleotide contained in pWT128. Primer sequences described by SEQ ID NO:22 and SEQ ID NO:24 were used to amplify the 410 bp promoter polynucleotide deletion region of p-47116125 contained in pAW222qcz. Primer sequences described by SEQ ID NO:23 and SEQ ID NO:24 were used to amplify the 210 bp promoter polynucleotide deletion region of p-47116125 contained in pAW222qcz.

The amplified DNA fragment size for each PCR product was verified by standard agarose gel electrophoresis and the DNA extracted Purified fragments were digested with PstI and AscI for the promoter polynucleotide deletions of At1g21460 amplified from pWT128 and PstI and AatII for the promoter polynucleotide deletions of p-47116125 amplified from pAW222qcz following the manufacturer's instructions (New England Biolabs, Ipswich, Massachusetts, US). The digested fragments were purified using the Qiagen PCR purification kit (Qiagen). The 499 bp promoter polynucleotide deletion region of At1g21460 promoter polynucleotide amplified using primers SEQ ID NO:19 and SEQ ID NO:21 is represented by bases 500 to 998 of SEQ ID NO:1. The 251 bp promoter polynucleotide deletion region of At1g21460 promoter polynucleotide amplified using primers SEQ ID NO:20 and SEQ ID NO:21 is represented by bases 748 to 998 of SEQ ID NO:1. The 410 bp promoter polynucleotide deletion region of p-47116125 promoter polynucleotide amplified using primers SEQ ID NO:22 and SEQ ID NO:24 is represented by bases 200 to 609 of SEQ ID NO:3. The 210 bp promoter polynucleotide deletion region of p-47116125 promoter polynucleotide amplified using primers SEQ ID NO:23 and SEQ ID NO:24 is represented by bases 400 to 609 of SEQ ID NO:3. The restriction sites introduced in the primers for facilitating cloning are not included in the designated sequences.

Example 5

Binary Vector Construction of At1g21460 and p-47116125 Promoter Polynucleotide Deletions for Transformation and Generation of Transgenic Hairy Roots To evaluate the expression activity of the cloned promoter polynucleotide deletions derived from pWT128 and pAW222qcz, gene fragments corresponding to nucleotides 500 to 998 of SEQ ID NO:1, 748 to 998 of SEQ ID NO:1, 200 to 609 of SEQ ID NO:3, and 400 to 609 of SEQ ID NO:3 were cloned upstream of a GUS reporter gene (bacterial β-glucuronidase or GUS gene to create the binary vectors RTJ113, RTJ114, RTJ117, and RTJ118, respectively. The plant selection marker in the binary vectors was a mutated AHAS gene from *A. thaliana* (Sathasivan et al., Plant Phys. 97:1044-50, 1991) that conferred tolerance to the herbicide ARSENAL (imazapyr, BASF Corporation, Florham Park, N.J.).

In the present example, binary vectors RTJL113, RTJL114, RTJL117, and RTJL118 were transformed into *A. rhizogenes* K599 strain by electroporation. Which in turn was used to create transgenic hary roots as described in Example 3. The transgenic hary roots were used for GUS-stainings to detect promoter polynucleotide activity as described in Example 3.

For each transgenic line, 10 randomly picked syncytia were observed and scored for intensity of GUS expression at 12 Days after infection (DAI). The following scoring index was used: "−" for no staining, "+" for weak staining, "++" for strong staining. A round-up average of the 10 counts was used to determine the GUS expression level in the syncytia for that line. In addition, GUS expression level in the same lines for other root tissues such as callus, root-tip, vasculature, cortical and primordial were also recorded using the same GUS scoring index of "−" for no staining, "+" for weak staining, "++" for strong staining. The results for lines transformed with pWT128, RTJ113, and RTJ114 presented in FIG. 9. The results for lines transformed with pAW222qcz, RTJ117, and RTJ118 are presented in FIG. 10.

The 499 and 251 bp promoter polynucleotide fragments of the At1g21460 promoter polynucleotide contained in RTJ113 and RTJ114, respectively, were both able to confer nematode-induced expression in syncytia, indicating that all of the required regulatory elements to result in nematode-induced expression are contained in the 251 bp promoter polynucleotide contained in RTJ114. The results indicate that there is more vascular tissue expression in the 499 and 251 bp promoter polynucleotide fragments of the At1g21460 promoter contained in RTJ113 and RTJ114, respectively, compared to pWT128 promoter sequence.

The 410 and 210 bp promoter polynucleotide fragments of the p-47116125 promoter polynucleotide contained in RTJ117 and RTJ118, respectively, were both able to confer nematode-induced expression in syncytia, indicating that all of the required regulatory elements to result in nematode-induced expression are contained in the 210 bp promoter polynucleotide fragmentcontained in RTJ118. The results indicate that there is less vascular tissue expression in the 210 bp promoter polynucleotide fragment of the p-47116125 promoter contained in RTJ114 compared to pAW222qcz promoter sequence.

Example 6

PLACE Analysis of Promoter Polynucleotides

PLACE (National Institute of Agrobiological Sciences, Ibaraki, Japan) analysis results indicate a TATA box localized at nucleotide position 830 to nucleotide position 836 of SEQ ID NO:1 as shown in FIG. 1. According to TAIR website information, the 5' untranslated region starts at about nucleotide position 923. The sequence described by SEQ ID NO:1 ends immediately before the ATG start codon. The potential core region of the promoter polynucleotide described by SEQ ID NO:1 is from nucleotide position 573 to nucleotide position 922.

PLACE analysis results indicate no TATA box localized within about 300 bp of the 3' end of SEQ ID NO:2 as shown in FIG. 2. The predicted 5' untranslated region is unknown.

The sequence described by SEQ ID NO:2 ends immediately before the ATG start codon. The potential core region of the promoter polynucleotide described by SEQ ID NO:2 is from nucleotide position 986 to nucleotide position 1637.

PLACE results indicate a TATA box localized at nucleotide position 513 to nucleotide position 519 of SEQ ID NO:3 as shown in FIG. 3. In consequence, the 5' untranslated region starts at about nucleotide position 553. The sequence described by SEQ ID NO:3 ends immediately before the ATG start codon. The potential core region of the promoter polynucleotide described by SEQ ID NO:3 is from nucleotide position 260 to nucleotide position 609.

Example 7

Binary Vector Construction to Generate Whole Plant Promoter Polynucleotide Constructs with BAR Selection To evaluate the expression activity of the cloned promoter polynucleotides represented by nucleotides from position 250 to 998 of SEQ ID NO:1 and nucleotides from position 1 to 609 of SEQ ID NO:3 in soybean nodules after *Bradyrhizobium japonicum* infection and fungal inoculation with *Rhizoctonia solani* form a specialis (f. sp.) glycines and *Fusarium solani* f. sp. glycines, promoter polynucleotides represented by nucleotides from position 250 to 998 of SEQ ID NO:1 and nucleotides from position 1 to 609 of SEQ ID NO:3 were cloned upstream of a GUS reporter gene (bacterial β-glucuronidase or GUS gene) to create the binary vectors RTJ125 and RTJ129, respectively. The plant selection marker in the binary vectors is a BAR gene (De Block, M. et. al. (1987) EMBO J.6:2513-2518) driven by the constitutive nopaline synthase gene promoter (p-NOS, An G. at al., The Plant Cell 3:225-233, 1990). Binary vectors RTJ125 and RTJ129 were used to generate transgenic roots for analysis.

Example 8

Soybean Rooted Plant Assay System

This assay can be found in co-pending application U.S. Ser. No. 60/871,258 filed on December 21, 2006, hereby incorporated by reference, and by the description that follows.

Clean soybean seeds from soybean cultivar were surface sterilized and germinated. The resulting soybean seedlings had elongated hypocotyls with visible epicotyls. The explants were prepared by removing the epicotyls and part of the hypocotyls. The explant contained one or two cotyledons, an axillary meristem and the hypocotyl. The seed coat was removed to facilitate cotyledon development. The cut end of the hypocotyl was the target for transformation/infection. Three days before inoculation, an overnight liquid culture of the disarmed Agrobacterium culture, for example, the disarmed *A. rhizogenes* strain K599 containing the binary vector was initiated. The next day the culture was spread onto an LB agar plate containing kanamycin as a selection agent. The plates were incubated at 28° C. for two days. One plate was prepared for every 50 explants to be inoculated. The prepared explants were dipped onto the disarmed thick *A. rhizogenes* colonies prepared above so that the colonies were visible on the cut end surface. The explants were then placed onto 1% agar in Petri dishes for co-cultivation under light for 6-8 days. After the transformation and co-cultivation soybean explants were transferred to rooting induction medium with a selection agent, for example S-B5-607 for Bar gene selection (De Block et al., EMBO J. 6:2513-2518, 1987). The S-MS-607 medium comprises: 0.2×MS salts and B5 vitamins, 2% sucrose, 400 mg/l Timentin, and 3 mg/L Glufosinate Ammonium at pH5.8. Explants were maintained in the same condition as in the co-cultivation step. Two to three weeks after the selection and root induction, transformed roots were formed on the cut ends of the explants. Explants were transferred to the same selection medium (S-B5-607 medium) for further selection. Transgenic roots proliferated well within one week in the medium and were ready to be subcultured.

Example 9

Rooted Plant Assay System Nodule Induction and Detection of Promoter Polynucleotide Activity in Nodules As set forth in Example 7, the promoter polynucleotides of the invention were placed in operative association with the GUS reporter gene to determine expression activity. The 1-glucuronidase activity of the GUS gene can be detected in planta by means of a chromogenic substance such as 5-bromo-4-chloro-3-indoyl-β-D-glucuronic acid (x-Gluc) in an activity staining reaction (Jefferson, supra).

In the present example, binary vectors RTJ125 and RTJ129 were transformed into the disarmed *A. rhizogenes* K599 strain SHA017 (pSB1) by electroporation. The transformed *Agrobacterium* was used to induce soybean root formation using the protocol outlined in Examples 8 using the cut end of the hypocotyl as the target for *Agrobacterium* transformation/infection. Rooted explants were removed from the elongation media and the roots were washed with water to remove excess media. The entire explants were transferred to 4 inch pots containing wet sand. The explants were watered every 2 days with Buffered Nodulation Medium (Ehrhardt et al., 1992). After two days in wet sand, the explant roots were inoculated with *Bradyrhizobium japonicum*.

For this, a 4 ml *Bradyrhizobium japonicum* culture was started in YM liquid media and grown at 28 C with shaking. YM media contains per liter: 10g Mannitol, 0.4 g yeast extract, 1 ml K2HPO4 (10% w/v stock), 4 ml KH2PO4 (10% w/v stock), 1 ml NaCl (10% w/v stock), and 2 ml MgSO4.7H20 (10% w/v stock). The pH was adjusted to 6.8 and the 1 liter final volume solution was autoclaved. After 7 days, 600 microliters of the starter culture was transferred to 40 ml of fresh YM liquid media. Multiple 40 ml cultures were started. The cultures grew for 48 hours at 28 C with shaking to an OD600 of approximately 0.2. The *Bradyrhizobium japonicum* cultures were combined and diluted 6 fold with Buffered Nodulation Medium. Each pot containing a rooted explant was inoculated with approximately 25 ml of the diluted *Bradyrhizobium japonicum* culture. Approximately 4 holes about 2 inches deep were created in the sand using a wooden dowel and the diluted *Bradyrhizobium japonicum* culture was inoculated into the holes using a pipette. Beginning the day after inoculation, the rooted explants were watered with Buffered Nodulation Medium every 2 days.

After 2 weeks, the rooted explants were removed from the 4 inch pots and the roots were washed with water to remove sand. Regions of root containing nodules were dissected using a razor blade and placed into GUS staining solution containing X-Gluc (2 mg/l) and then transferred to 37° C. for 16 hours. Some nodules were sliced in half using a razor blade. The GUS staining solution was removed and replaced with a solution containing equal parts of glycerol, water, and acetic acid. The root nodules were then observed for GUS staining. It was observed that the promoter polynucleotides described by bp 250 to 998 of SEQ ID NO:1 contained in construct RTJ125 did induce GUS expression in root nodules. It was observed that the promoter polynucleotide described by SEQ ID NO:3 contained in RTJ129 did induce GUS expression in root nodules to a small extent in some nodules observed at the base of the nodule.

Example 10

Rooted Plant Assay Detection of Promoter Polynucleotide Activity in Fungi Inoculated Roots As set forth in Example 7, the promoters polynucleotides of the invention were placed in operative association with the GUS reporter gene to determine expression activity. The β-glucuronidase activity of the GUS gene can be detected in planta by means of a chromogenic substance such as 5-bromo-4-chloro-3-indoyl-β-D-glucuronic acid (x-Gluc) in an activity staining reaction.

In the present example, binary vectors RTJ125 and RTJ129 were transformed into the disarmed *A. rhizogenes* K599 strain SHA017 (pSB1) by electroporation. The transformed *Agrobacterium* was used to induce soybean root formation using the protocol outlined in Example 8.

To study the promoter polynucleotide activity of bp 250 to 998 of SEQ ID NO:1 and bp 1 to 609 of SEQ ID NO:3 after inoculation with either *Rhizoctonia solani* f. sp. glycines or *Fusarium solani* f. sp. glycines, several independent transgenic lines were generated from transformation with constructs RTJ125 and RTJ129, respectively. Subcultured root lines were inoculated with *Rhizoctonia solani* f. sp. glycines or *Fusarium solani* f. sp. Glycines by placing a small amount of hypha adjacent to several roots using tweezers. At 3 days after inoculation (DAI), the roots were removed from the agar plates and stained in GUS staining solution containing X-Gluc (2 mg/l) at 37° C. for 16 hours. The roots were then observed under a microscope for detection of GUS expression.

For each transgenic line, roots were observed and the intensity of GUS expression at 3 days after infection (DAI) was noted. It was observed that the promoter polynucleotide described by bp 250 to 998 of SEQ ID NO:1 contained in construct RTJ125 did not induce GUS expression in roots after inoculation with *Rhizoctonia solani* f. sp. glycines and *Fusarium solani* f. sp. glycines. It was observed that the promoter polynucleotide described by SEQ ID NO:3 contained in construct RTJ129 did not induce GUS expression in roots after inoculation with *Rhizoctonia solani* f. sp. glycines or *Fusarium solani* f. sp. glycines.

Example 11

Rooted Plant Assay Transformation with RCB1022 for GUS Staining Analysis

In the present example, binary vector RCB1022 will be transformed into the disarmed *A. rhizogenes* SHA017 strain by electroporation. The transformed *Agrobacterium* will be used to induce soybean TRAP root formation using protocol as outlined by Example 8. Multiple lines of soybean TRAP roots generated using disarmed *Agrobacterium* transformed with construct RCB1022. TRAP root lines will be inoculated with surface-decontaminated J2 of SCN race 3 at the 2000 J2/plate level. At 12 days after inoculation (DAI), the roots will be harvested by removing from the agar plates and gently rinsed with changes in water and stained in GUS staining solution containing X-Gluc (2 mg/l) at 37° C. for 16 hours. A non-inoculated control plate from each line will also be stained in GUS staining solution. The roots will then observed under a microscope for detection of GUS expression.

For each transgenic line, 10 randomly picked syncytia will be observed and scored for intensity of GUS expression at 12 Days after infection (DAI). The following scoring index will be used: "−" for no staining, "+" for weak staining, "++" for strong staining. A round-up average of the 10 counts will be used to determine the GUS expression level in the syncytia for that line. In addition, GUS expression level in the same lines for other root tissues such as callus, root-tip, vasculature, cortical and primordial will also be recorded using the same GUS scoring index of "−" for no staining, "+" for weak staining, "++" for strong staining.

Example 12

Whole Plant GUS Staining

Transgenic soybean whole plants are generated by transforming constructs comprising the promoter polynucleotide represented by nucleotides from position 250 to 998 of SEQ ID NO:1, nucleotides from position 500 to 998 of SEQ ID NO:1, nucleotides from position 748 to 998 of SEQ ID NO:1, nucleotides from position 1 to 609, of SEQ ID NO:3, nucleotides from position 200 to 609 of SEQ ID NO:3, nucleotides from position 400 to 609 of SEQ ID NO:3, or nucleotides from position 1 to 1986 of SEQ ID NO:2 in operative association with the GUS reporter gene to characterize promoter polynucleotide expression in response to nematode infection in roots and whole plant tissues throughout the plant life cycle. Representative methods of promoter polynucleotide characterization in soybean whole plants include, but are not limited to, the following descriptions. Transgenic soybean T1 seeds are tested for zygosity and single copy events are germinated, grown in greenhouse conditions, and sampled for GUS expression at various stages of development in leaf, stem, flower, embryo, and seed pod tissues. In addition, root tissues are harvested at various times before and after SCN infection in inoculated and un-inoculated control roots. Multiple plants are tested for each event to determine consistent trends in the GUS staining analysis. Harvested samples are cut off of the plant and immediately placed into GUS staining solution containing X-Gluc (2 mg/l), vacuum infiltrated for 20 minutes, and transferred to 37° C. for 16 hours. The tissues are then observed and scored for the intensity of GUS staining.

What is claimed is:

1. An isolated promoter comprising a polynucleotide selected from the group consisting of:
   a) a polynucleotide comprising nucleotides 1 to 609 of SEQ ID NO: 3; and
   b) a polynucleotide comprising nucleotides 400 to 609, or nucleotides 260 to 609, or nucleotides 200 to 609 of SEQ ID NO:3.

2. The promoter of claim 1, wherein the polynucleotide comprises nucleotides 400 to 609, or nucleotides 260 to 609, or nucleotides 200 to 609 of SEQ ID NO:3.

3. An expression cassette comprising a promoter polynucleotide selected from the group consisting of:
   a) a polynucleotide comprising nucleotides 1 to 609 of SEQ ID NO: 3; and
   b) a polynucleotide comprising nucleotides 400 to 609, or nucleotides 260 to 609, or nucleotides 200 to 609 of SEQ ID NO:3, and
which further comprises one or more operably linked polynucleotides.

4. The expression cassette of claim 3, wherein said one or more operably linked polynucleotides encode an agent that disrupts metabolism, growth, or reproduction of a plant parasitic nematode, that confers or improves plant resistance to a plant parasitic nematode, or that is toxic to a plant parasitic nematode.

5. A transgenic plant transformed with an expression cassette, wherein the expression cassette comprises a promoter comprising a polynucleotide selected from the group consisting of:
- a), a polynucleotide comprising nucleotides 1 to 609 of SEQ ID NO: 3; and
- b) a polynucleotide comprising nucleotides 400 to 609, or nucleotides 260 to 609, or nucleotides 200 to 609 of SEQ ID NO:3.

6. The transgenic plant of claim 5, wherein the expression cassette further comprises one or more polynucleotides operably linked to the promoter.

7. The transgenic plant of claim 5, wherein the plant is selected from the group consisting of maize, wheat, barley, sorghum, rye, triticale, rice, sugarcane, citrus trees, pineapple, coconut, banana, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, *Lotus* sp., *Medicago truncatula*, perennial grass, ryegrass, and *Arabidopsis thaliana*.

8. The transgenic plant of claim 5, wherein the isolated promoter polynucleotide comprises nucleotides 400 to 609, or nucleotides 260 to 609, or nucleotides 200 to 609 of SEQ ID NO:3.

9. The promoter of claim 1, wherein the polynucleotide comprises nucleotides 1 to 609 of SEQ ID NO:3.

10. The transgenic plant of claim 5, wherein the promoter comprises nucleotides 1 to 609 of SEQ ID NO:3.

* * * * *

```
                        SEQUENCE LISTING

<160> NUMBER OF SEQ ID NOS: 45

<210> SEQ ID NO 1
<211> LENGTH: 998
<212> TYPE: DNA
<213> ORGANISM: Arabidopsis thaliana

<400> SEQUENCE: 1
ctccggttaa aatgatcatg aatgaaccga tatggtttgg gtaaagctga ataagctaac     60
tcgtggtgac tagaaaacat tccaaaaaga tcactcacta tactaaaaag tatatcctgc    120
ggctgtggtt caacggtata gaataactga aatttagtga aacttattgg tgcccttaaa    180
taaacttgac agtttgttag gtttggtttc gcttatgtaa ccagaaactt cctaaactgt    240
caaattttat ctagaatctc tattaaagag ggcaacgaaa aaaaaaagt aacacatcat     300 ggagaagatg aaccactagc cactgccccg cagaaaatac aggctcgggc ctcgagtcac    360
atatcaacgt caagcccaga acactctggc ttgttcagag ctactttag tatcaaacaa     420 aaaacaaaag aagaaaagac attgctcttt ttaggtgttt atttcatttt taagtattta    480
accatatctc tataactatc tacaaaagaa acgtcgatcc aaagagtcag gttcacctct    540
cgaggacgta aaaacaagta acagataaaa aacctcgttc caaaaattaa tttggtatca    600
agaaaaaatc tgtatatata cactagaatt caaaatcatg ggaactttt tttttttat     660 aagaaataac tcaattaact caaatttaaa acttaggttt tctcaaaaca ttagttctta    720
accataactt ttttttcaaa ttttattcat actacaaaaa ttaataacag aaccatgtat    780
ttttaaaatt taatatttaa taccattatt tcataattta ttatactttt attaattttg    840
taattattgg tgttccacag tgaagcggtt aacacacgct gaatctcgat atatatacgc    900
ttgccgatag aaaacactta gctcatattc tctcactttc tctctcagct tacgaacaag    960
aaaaaaagaa gaatctttag ccacctttga gatcaaaa                            998

<210> SEQ ID NO 2
<211> LENGTH: 1986
<212> TYPE: DNA
<213> ORGANISM: Arabidopsis thaliana

<400> SEQUENCE: 2
cgactgtctc atcatttgtg attttttttt gccagtactt tatttttttt ggtaaactag     60
attggtctta taacttataa gttataacaa aatcacatcc ctctgtaaat ttatttattt    120
taactttaac caaaaaatca aaagaataag ttgtgctgtg ttgaggacaa attttataat    180
aaagaaataa ggacacgaag gaagaatgga agtccttgct agttggtgcc atttccaata    240
cgattccaac aacttagcca acttttttttt tttttttttt ttttgataaa gaacacctta    300
gccaacttac gaaaagtttc taactctttc gttcttttatt agttctatat gtattaatgc    360
```

```
atgcattatt gtgaccaaaa agtatatatt aaataaaaaa tgtatatttt catgtaattt      420
tgtttgtaat attatttatt ttagttttat aaattcaccg tattctatta gttcgctagg      480
ttcttgaaac tcaaaatttg attcttgagt gatatatggt aatctagcaa ctcgaattag      540
cctgtaaatt aatttagaac aatgtaaaga tttcatgttt ttacgtataa attacatgtt      600
tgcaaattaa ttagtttgga ttttggtata taaatgagga tattttcatt catttaagtg      660
ttttgatgtt gagaaaacat aggtataaat gatgaatata taacaccaac atcataattg      720
ttagtaaata ttcatttgaa aagagtgaga tcagaaattg attgataagg aagagacaat      780 acaaagaga tggaaaatga actaagtaaa ccataagcat aactggatgt gcatttcaag       840
cataatttgg ctcaaaacta aatttataat taaaatagat aatcctaatt ttttgacaag      900
attttttttt tgttgagaaa atgtttataa tatacaaagt tcttgataaa ggacactagt      960
ttcacacccc acgtgttgct aaccggccac cacaaagcta acttaaaaat gtttttaact     1020
tttttaattg gagttccttt ttatctccat gcattattat cattttctat tatatattcc     1080
ataagcactt aaacaaatca gtcttcttta ttcgattcgg aatttaatgt gatacaaaca     1140
aaataatcaa agttttgtg tgtatatccg tttaaaaaaa gggagatttg tgtgtacgat      1200
ttggatcaag ccttttgcg catcaaaatt gtcacttgca gacgttaatg tgcccgttag      1260
accttcacaa tctattaaac taataatttt aaaaaatttc tattactgga tatatatata     1320
tatatatata taacgttaa taatcaggta aaattacttt cgtaaaaaca aaaaacaaaa      1380
aatgatttac aaatttggtt ttgtaagata tatatatata tatatatata tatatgcgtt     1440
tgtaatttgg gatggaatgg ttgctaatag gttgttgaat cacataattt gtgtgatata     1500
tcatctagtg ttatacgtgt atataagttt gtgtaagaca ttgtatatat aaacaactta     1560
atctccacac acgtctaata atgtcatata tatggtctga taactccaag aacttgaaat     1620
tagatttagt aaactcaaga aatgaacaac catctttcta ggttcgtttc tagttaatga     1680
aacatccgtg tatgaaaatt atatgttatt ctaaaatttc cagtagtttt tctaattcaa     1740
gcttggtctc tatgttttag aaaaaaagaa aaacttagag aagcaattgt tatttatctc     1800
atcacaccaa tataattttt ggaaccaaat tgttaaatta ccaaatgtcc caaacttgtg     1860
atcaaattta gatgattatt tttaaatgaa cattaaagaa aaactattat atatatacac     1920
acccattata gacgtaactc tactgcttcc aacttttccc taatctttgt tcttccggcc     1980
aatcaa                                                                1986

<210> SEQ ID NO 3
<211> LENGTH: 609
<212> TYPE: DNA
<213> ORGANISM: Glycine max

<400> SEQUENCE: 3
gaagccacgt catgaagagt atatcatttc agtaatgttt tgagacgcct ctataatgct       60
ttaccaacaa aacaaaacaa aaaaagaac atttgaaacc atttgtatta aaaaaaaaa       120 ggtatattag gccataatat tataggtaac atgaaatatc aaatgacacg caagagtttt      180
gtcaaaaatg aaaccatcac acatcagaga ttatggcaaa taatgttttg tgtgtctctt      240
gcttcaccca taacataagc ctctataact ggagagaaga aaaaaaaaag tggagggct       300 agggtgggaa tttggaagaa tacagttata ttgagcattg agcaagttga tagaaagctt      360
ctcaatttgt acaaaatttg catccacatg attattaaag acgtagacag cacttcttcc     420 ttctttttt ctataagttt cttatatatt gttcttcatg ttttaatatt attactttat       480
```

```
gtacgcgtct aacagtagtc ctcccaaact gctataaata gagcctcttc aacgcacctc      540
ttggcagtac aaaaattatt catctcttct aagttctaat tttctaagca ttcagtaaaa      600
gaactaacc                                                              609
```

<210> SEQ ID NO 4
<211> LENGTH: 956
<212> TYPE: DNA
<213> ORGANISM: Glycine max
<400> SEQUENCE: 4

```
gcattcagta aaagaactaa acatggcaga gaccattcgt ttggctgttg ctgttcttgg       60
caatgcagcc tcagttgccc tttatgctgc accaatggtt accttagaa gagttataag      120 gaagaaaagc acagaggagt tttcatgctt tccttacatc attggcctct tgaattgtct      180
ccttttcact tggtacggtt tgcctgttgt gagttacaag tgggaaaatt ccctctcgt      240 cacagttaat ggagttggta ttgttctcga gttatcctat gttctcattt acttctggta      300
tgcttcagcc aaaggaaagg tgaaggtagc catgactgca ataccagttt gctggtgtt       360 ctctataatt gctgcagtgt cagcttttgc attccatgat aatcatcacc ggaagcttct      420
cgtaggtagc atcggcttag gtgtttcagt aacaatgtat ggatccccctt tgattgtaat    480 gaagaaagtt atacaaacca agagtgtgga attcatgcca ctaccgttat ccatgtgctc      540 attttttagcc actgttctct ggctgattta tggacttctc attcgtgata tattcgttgc    600
gggtcctagt gcggttggaa ctcccttggg gatcttgcaa cttgtacttt actgtaaata     660
ccgaaaaggg agtgttgtgg aggatccaag taaggggggac cttgagaagg gtaacttgga   720
gaaggtggaa atggaaattg ggaaagtgga atgaatgtc acgaatcaca tgaacggaca      780
ctcgtgaaca atgcgtctaa ggggaaagat tgaagattac agaatgttct attcagattc      840
cttcttttta tgttttattt cctttatttt aagacaaaat gatccccct tagctttggt      900 tgtattgctc acatataaat taagttatat tacttcccaa aaaaaaaaaa aaaaaa         956
```

<210> SEQ ID NO 5
<211> LENGTH: 254
<212> TYPE: PRT
<213> ORGANISM: Glycine max
<400> SEQUENCE: 5

```
Met Ala Glu Thr Ile Arg Leu Ala Val Ala Val Leu Gly Asn Ala Ala
1               5                   10                  15

Ser Val Ala Leu Tyr Ala Ala Pro Met Val Thr Phe Arg Arg Val Ile
            20                  25                  30

Arg Lys Lys Ser Thr Glu Glu Phe Ser Cys Phe Pro Tyr Ile Ile Gly
        35                  40                  45

Leu Leu Asn Cys Leu Leu Phe Thr Trp Tyr Gly Leu Pro Val Val Ser
    50                  55                  60

Tyr Lys Trp Glu Asn Phe Pro Leu Val Thr Val Asn Gly Val Gly Ile
65                  70                  75                  80

Val Leu Glu Leu Ser Tyr Val Leu Ile Tyr Phe Trp Tyr Ala Ser Ala
                85                  90                  95

Lys Gly Lys Val Lys Val Ala Met Thr Ala Ile Pro Val Leu Leu Val
            100                 105                 110

Phe Ser Ile Ile Ala Ala Val Ser Ala Phe Ala Phe His Asp Asn His
        115                 120                 125

His Arg Lys Leu Leu Val Gly Ser Ile Gly Leu Gly Val Ser Val Thr
```

```
            130                 135                 140
Met Tyr Gly Ser Pro Leu Ile Val Met Lys Lys Val Ile Gln Thr Lys
145                 150                 155                 160

Ser Val Glu Phe Met Pro Leu Pro Leu Ser Met Cys Ser Phe Leu Ala
                165                 170                 175

Thr Val Leu Trp Leu Ile Tyr Gly Leu Leu Ile Arg Asp Ile Phe Val
            180                 185                 190

Ala Gly Pro Ser Ala Val Gly Thr Pro Leu Gly Ile Leu Gln Leu Val
                195                 200                 205

Leu Tyr Cys Lys Tyr Arg Lys Gly Ser Val Val Glu Asp Pro Ser Lys
            210                 215                 220

Gly Asp Leu Glu Lys Gly Asn Leu Glu Lys Val Glu Met Glu Ile Gly
225                 230                 235                 240

Lys Val Glu Met Asn Val Thr Asn His Met Asn Gly His Ser
                245                 250

<210> SEQ ID NO 6
<211> LENGTH: 247
<212> TYPE: PRT
<213> ORGANISM: Arabidopsis thaliana

<400> SEQUENCE: 6

Met Asn Ile Ala His Thr Ile Phe Gly Val Phe Gly Asn Ala Thr Ala
1               5                   10                  15

Leu Phe Leu Phe Leu Ala Pro Ser Ile Thr Phe Lys Arg Ile Ile Lys
                20                  25                  30

Asn Lys Ser Thr Glu Gln Phe Ser Gly Ile Pro Tyr Pro Met Thr Leu
            35                  40                  45

Leu Asn Cys Leu Leu Ser Ala Trp Tyr Gly Leu Pro Phe Val Ser Lys
    50                  55                  60

Asp Asn Thr Leu Val Ser Thr Ile Asn Gly Thr Gly Ala Val Ile Glu
65                  70                  75                  80

Thr Val Tyr Val Leu Ile Phe Leu Phe Tyr Ala Pro Lys Lys Glu Lys
                85                  90                  95

Ile Lys Ile Phe Gly Ile Phe Ser Cys Val Leu Ala Val Phe Ala Thr
            100                 105                 110

Val Ala Leu Val Ser Leu Phe Ala Leu Gln Gly Asn Gly Arg Lys Leu
        115                 120                 125

Phe Cys Gly Leu Ala Ala Thr Val Phe Ser Ile Ile Met Tyr Ala Ser
130                 135                 140

Pro Leu Ser Ile Met Arg Leu Val Val Lys Thr Lys Ser Val Glu Phe
145                 150                 155                 160

Met Pro Phe Phe Leu Ser Leu Phe Val Phe Leu Cys Gly Thr Ser Trp
                165                 170                 175

Phe Val Tyr Gly Leu Ile Gly Arg Asp Pro Phe Val Ala Ile Pro Asn
            180                 185                 190

Gly Phe Gly Cys Ala Leu Gly Thr Leu Gln Leu Ile Leu Tyr Phe Ile
        195                 200                 205

Tyr Cys Gly Asn Lys Gly Glu Lys Ser Ala Asp Ala Gln Lys Asp Glu
    210                 215                 220

Lys Ser Val Glu Met Lys Asp Asp Glu Lys Gln Asn Val Val Asn
225                 230                 235                 240

Gly Lys Gln Asp Leu Gln Val
                245
```

```
<210> SEQ ID NO 7
<211> LENGTH: 263
<212> TYPE: PRT
<213> ORGANISM: Arabidopsis thaliana

<400> SEQUENCE: 7

Met Gly Asp Lys Leu Arg Leu Ser Ile Gly Ile Leu Gly Asn Gly Ala
1               5                   10                  15

Ser Leu Leu Leu Tyr Thr Ala Pro Ile Val Thr Phe Ser Arg Val Phe
                20                  25                  30

Lys Lys Lys Ser Thr Glu Glu Phe Ser Cys Phe Pro Tyr Val Met Thr
            35                  40                  45

Leu Phe Asn Cys Leu Ile Tyr Thr Trp Tyr Gly Leu Pro Ile Val Ser
    50                  55                  60

His Leu Trp Glu Asn Leu Pro Leu Val Thr Ile Asn Gly Val Gly Ile
65                  70                  75                  80

Leu Leu Glu Ser Ile Phe Ile Phe Ile Tyr Phe Tyr Tyr Ala Ser Pro
                85                  90                  95

Lys Glu Lys Ile Lys Val Gly Val Thr Phe Val Pro Val Ile Val Gly
            100                 105                 110

Phe Gly Leu Thr Thr Ala Ile Ser Ala Leu Val Phe Asp Asp His Arg
        115                 120                 125

His Arg Lys Ser Phe Val Gly Ser Val Gly Leu Val Ala Ser Ile Ser
130                 135                 140

Met Tyr Gly Ser Pro Leu Val Val Met Lys Lys Val Ile Glu Thr Arg
145                 150                 155                 160

Ser Val Glu Tyr Met Pro Phe Tyr Leu Ser Phe Ser Phe Leu Ala
                165                 170                 175

Ser Ser Leu Trp Leu Ala Tyr Gly Leu Leu Ser His Asp Leu Phe Leu
                180                 185                 190

Ala Ser Pro Asn Met Val Ala Thr Pro Leu Gly Ile Leu Gln Leu Ile
            195                 200                 205

Leu Tyr Phe Lys Tyr Lys Asn Lys Lys Asp Leu Ala Pro Thr Thr Met
        210                 215                 220

Val Ile Thr Lys Arg Asn Asp His Asp Asp Lys Asn Lys Ala Thr Leu
225                 230                 235                 240

Glu Phe Val Val Asp Val Asp Arg Asn Ser Asp Thr Asn Glu Lys Asn
                245                 250                 255

Ser Asn Asn Ala Ser Ser Ile
            260

<210> SEQ ID NO 8
<211> LENGTH: 1127
<212> TYPE: DNA
<213> ORGANISM: Glycine max

<400> SEQUENCE: 8
actatagggc acgcgtggtc gacggcccgg gctggtatct ctacaaaatg gaagccacgt      60
catgaagagt atatcatttc agtaatgttt tgagacgcct ctataatgct ttaccaacaa     120
aacaaaacaa aaaaaagaac atttgaaacc atttgtatta aaaaaaaaaa ggtatattag     180
gccataatat tataggtaac atgaaatatc aaatgacacg caagagtttt gtcaaaaatg     240
aaaccatcac acatcagaga ttatggcaaa taatgttttg tgtgtctctt gcttcaccca     300
taacataagc ctctataact ggagagaaga aaaaaaaaag tggagggggct agggtgggaa     360 tttggaagaa tacagttata ttgagcattg agcaagttga tagaaagctt ctcaatttgt     420
```

-continued

| | |
|---|---|
| acaaaatttg catccacatg attattaaag acgtagacag cacttcttcc ttcttttttt | 480 |
| ctataagttt cttatatatt gttcttcatg ttttaatatt attactttat gtacgcgtct | 540 |
| aacagtagtc ctcccaaact gctataaata gagcctcttc aacgcacctc ttggcagtac | 600 |
| aaaaattatt catctcttct aagttctaat tttctaagca ttcagtaaaa gaactaacca | 660 |
| tggcagagac cattcgcttg ggtgttgctg ttcttggtac ttcttcgttc attcattcct | 720 |
| tagctttgaa cgtatagggt gattaattat tattcattat ttgagtcttc aaaaaaagtg | 780 |
| actcattagt accactgttt gttttttttt tcttgcagg caatgcagcc tcagttgccc | 840 |
| tttatgctgc accaatgtat gttacatgtt acatatataa taacattgct gcccaaatgt | 900 |
| cctccccttt agagaatgaa taaagtgctg aacgcttttt catgcttttc atgttccagg | 960 |
| gttaccttta gaagagttat aaggaagaaa agcacagagg agttttcatg ctttccttac | 1020 |
| atcattggcc tcttgaactg tctccttttc acttggtacg gtttgcctat tgttagctac | 1080 |
| aagtgggaaa atttccctct cgtcacagtt aatggagttg gtattgt | 1127 |

<210> SEQ ID NO 9
<211> LENGTH: 27
<212> TYPE: DNA
<213> ORGANISM: Artificial
<220> FEATURE:
<223> OTHER INFORMATION: primer sequence

<400> SEQUENCE: 9
aactgcagct ccggttaaaa tgatcat         27

<210> SEQ ID NO 10
<211> LENGTH: 30
<212> TYPE: DNA
<213> ORGANISM: Artificial
<220> FEATURE:
<223> OTHER INFORMATION: primer sequence

<400> SEQUENCE: 10
aaggcgcgcc ttttgatctc aaaggtggct         30

<210> SEQ ID NO 11
<211> LENGTH: 30
<212> TYPE: DNA
<213> ORGANISM: Artificial
<220> FEATURE:
<223> OTHER INFORMATION: primer sequence

<400> SEQUENCE: 11
aattaattaa cgactgtctc atcatttgtg         30

<210> SEQ ID NO 12
<211> LENGTH: 32
<212> TYPE: DNA
<213> ORGANISM: Artificial
<220> FEATURE:
<223> OTHER INFORMATION: primer sequence

<400> SEQUENCE: 12
aaggcgcgcc ttgattggcc ggaagaacaa ag         32

<210> SEQ ID NO 13
<211> LENGTH: 22
<212> TYPE: DNA
<213> ORGANISM: Artificial
<220> FEATURE:
<223> OTHER INFORMATION: primer sequence

```
<400> SEQUENCE: 13
gtaatacgac tcactatagg gc                                            22

<210> SEQ ID NO 14
<211> LENGTH: 19
<212> TYPE: DNA
<213> ORGANISM: Artificial
<220> FEATURE:
<223> OTHER INFORMATION: primer sequence

<400> SEQUENCE: 14
actatagggc acgcgtggt                                                19

<210> SEQ ID NO 15
<211> LENGTH: 29
<212> TYPE: DNA
<213> ORGANISM: Artificial
<220> FEATURE:
<223> OTHER INFORMATION: primer sequence

<400> SEQUENCE: 15
caccagcaaa actggtattg cagtcatgg                                     29

<210> SEQ ID NO 16
<211> LENGTH: 31
<212> TYPE: DNA
<213> ORGANISM: Artificial
<220> FEATURE:
<223> OTHER INFORMATION: primer sequence

<400> SEQUENCE: 16
acaataccaa ctccattaac tgtgacgaga g                                  31

<210> SEQ ID NO 17
<211> LENGTH: 25
<212> TYPE: DNA
<213> ORGANISM: Artificial
<220> FEATURE:
<223> OTHER INFORMATION: primer sequence

<400> SEQUENCE: 17
ctgcaggaag ccacgtcatg aagag                                         25

<210> SEQ ID NO 18
<211> LENGTH: 30
<212> TYPE: DNA
<213> ORGANISM: Artificial
<220> FEATURE:
<223> OTHER INFORMATION: primer sequence

<400> SEQUENCE: 18
ggcgcgccgg ttagttcttt tactgaatgc                                    30

<210> SEQ ID NO 19
<211> LENGTH: 31
<212> TYPE: DNA
<213> ORGANISM: Artificial
<220> FEATURE:
<223> OTHER INFORMATION: primer sequence

<400> SEQUENCE: 19
acgtctgcag ctacaaaaga aacgtcgatc c                                  31

<210> SEQ ID NO 20
<211> LENGTH: 36
<212> TYPE: DNA
```

```
<213> ORGANISM: Artificial
<220> FEATURE:
<223> OTHER INFORMATION: primer sequence

<400> SEQUENCE: 20
acgtctgcag catactacaa aaattaataa cagaac                                    36

<210> SEQ ID NO 21
<211> LENGTH: 26
<212> TYPE: DNA
<213> ORGANISM: Artificial
<220> FEATURE:
<223> OTHER INFORMATION: primer sequence

<400> SEQUENCE: 21
acgtggcgcg cctttgatc tcaaag                                                26

<210> SEQ ID NO 22
<211> LENGTH: 26
<212> TYPE: DNA
<213> ORGANISM: Artificial
<220> FEATURE:
<223> OTHER INFORMATION: primer sequence

<400> SEQUENCE: 22
gcatctgcag cacatcagag attatg                                               26

<210> SEQ ID NO 23
<211> LENGTH: 27
<212> TYPE: DNA
<213> ORGANISM: Artificial
<220> FEATURE:
<223> OTHER INFORMATION: primer sequence

<400> SEQUENCE: 23
gcatctgcag gacgtagaca gcacttc                                              27

<210> SEQ ID NO 24
<211> LENGTH: 27
<212> TYPE: DNA
<213> ORGANISM: Artificial
<220> FEATURE:
<223> OTHER INFORMATION: primer sequence

<400> SEQUENCE: 24
gcttgacgtc ggttagttct tttactg                                              27

<210> SEQ ID NO 25
<211> LENGTH: 15
<212> TYPE: DNA
<213> ORGANISM: Artificial
<220> FEATURE:
<223> OTHER INFORMATION: IUPAC consensus sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 25
wndwmvnkmd agaan                                                           15
```

```
<210> SEQ ID NO 26
<211> LENGTH: 17
<212> TYPE: DNA
<213> ORGANISM: Artificial
<220> FEATURE:
<223> OTHER INFORMATION: IUPAC consensus sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (13)..(17)
<223> OTHER INFORMATION: n is a, c, g, or t

<400> SEQUENCE: 26
nnwmwhmwst tannnnn                                                    17

<210> SEQ ID NO 27
<211> LENGTH: 13
<212> TYPE: DNA
<213> ORGANISM: Artificial
<220> FEATURE:
<223> OTHER INFORMATION: IUPAC consensus sequence
<220> FEATURE:
<221> NAME/KEY: misc_feature
<222> LOCATION: (11)..(12)
<223> OTHER INFORMATION: n is a, c, g, or t

<400> SEQUENCE: 27
wmwactdttd nnh                                                        13

<210> SEQ ID NO 28
<211> LENGTH: 15
<212> TYPE: DNA
<213> ORGANISM: Artificial
<220> FEATURE:
<223> OTHER INFORMATION: IUPAC consensus sequence
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t

<400> SEQUENCE: 28
nbnntatawa whnnn                                                      15

<210> SEQ ID NO 29
<211> LENGTH: 11
<212> TYPE: DNA
<213> ORGANISM: Artificial
<220> FEATURE:
<223> OTHER INFORMATION: IUPAC consensus sequence
<220> FEATURE:
<221> NAME/KEY: misc_feature
<222> LOCATION: (10)..(11)
<223> OTHER INFORMATION: n is a, c, g, or t

<400> SEQUENCE: 29
hawhttawtn n                                                          11

<210> SEQ ID NO 30
<211> LENGTH: 17
<212> TYPE: DNA
```

```
<213> ORGANISM: Artificial
<220> FEATURE:
<223> OTHER INFORMATION: IUPAC consensus sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(7)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 30
dnwrnnntta adwdhdn                                                    17

<210> SEQ ID NO 31
<211> LENGTH: 19
<212> TYPE: DNA
<213> ORGANISM: Artificial
<220> FEATURE:
<223> OTHER INFORMATION: IUPAC consensus sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 31
nnaamwnwnn dnwnwnrrd                                                  19

<210> SEQ ID NO 32
<211> LENGTH: 11
<212> TYPE: DNA
<213> ORGANISM: Artificial
<220> FEATURE:
<223> OTHER INFORMATION: IUPAC consensus sequence
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 32
nnnatdatta n                                                          11

<210> SEQ ID NO 33
<211> LENGTH: 17
<212> TYPE: DNA
```

```
<213> ORGANISM: Artificial
<220> FEATURE:
<223> OTHER INFORMATION: IUPAC consensus sequence
<220> FEATURE:
<221> NAME/KEY: misc_feature
<222> LOCATION: (15)..(15)
<223> OTHER INFORMATION: n is a, c, g, or t

<400> SEQUENCE: 33
dwwdwhwaam wbwanwd                                                  17

<210> SEQ ID NO 34
<211> LENGTH: 15
<212> TYPE: DNA
<213> ORGANISM: Artificial
<220> FEATURE:
<223> OTHER INFORMATION: IUPAC consensus sequence

<400> SEQUENCE: 34
wraaavttwd agaad                                                    15

<210> SEQ ID NO 35
<211> LENGTH: 17
<212> TYPE: DNA
<213> ORGANISM: Artificial
<220> FEATURE:
<223> OTHER INFORMATION: IUPAC consensus sequence
<220> FEATURE:
<221> NAME/KEY: misc_feature
<222> LOCATION: (16)..(16)
<223> OTHER INFORMATION: n is a, c, g, or t

<400> SEQUENCE: 35
rramwacwst takmynh                                                  17

<210> SEQ ID NO 36
<211> LENGTH: 13
<212> TYPE: DNA
<213> ORGANISM: Artificial
<220> FEATURE:
<223> OTHER INFORMATION: IUPAC consensus sequence

<400> SEQUENCE: 36
wmwactdtta kwh                                                      13

<210> SEQ ID NO 37
<211> LENGTH: 15
<212> TYPE: DNA
<213> ORGANISM: Artificial
<220> FEATURE:
<223> OTHER INFORMATION: IUPAC consensus sequence

<400> SEQUENCE: 37
hydhtatawa tabrs                                                    15

<210> SEQ ID NO 38
<211> LENGTH: 11
<212> TYPE: DNA
<213> ORGANISM: Artificial
<220> FEATURE:
<223> OTHER INFORMATION: IUPAC consensus sequence

<400> SEQUENCE: 38
waawttawtm h                                                        11

<210> SEQ ID NO 39
<211> LENGTH: 17
<212> TYPE: DNA
```

```
<213> ORGANISM: Artificial
<220> FEATURE:
<223> OTHER INFORMATION: IUPAC consensus sequence
<220> FEATURE:
<221> NAME/KEY: misc_feature
<222> LOCATION: (2)..(2)
<223> OTHER INFORMATION: n is a, c, g, or t

<400> SEQUENCE: 39
wnwrdtwtta awwdwwv                                                    17

<210> SEQ ID NO 40
<211> LENGTH: 19
<212> TYPE: DNA
<213> ORGANISM: Artificial
<220> FEATURE:
<223> OTHER INFORMATION: IUPAC consensus sequence

<400> SEQUENCE: 40
kraaatwakr rywtwraak                                                  19

<210> SEQ ID NO 41
<211> LENGTH: 11
<212> TYPE: DNA
<213> ORGANISM: Artificial
<220> FEATURE:
<223> OTHER INFORMATION: IUPAC consensus sequence
<220> FEATURE:
<221> NAME/KEY: misc_feature
<222> LOCATION: (11)..(11)
<223> OTHER INFORMATION: n is a, c, g, or t

<400> SEQUENCE: 41
ymratdatta n                                                          11

<210> SEQ ID NO 42
<211> LENGTH: 17
<212> TYPE: DNA
<213> ORGANISM: Artificial
<220> FEATURE:
<223> OTHER INFORMATION: IUPAC consensus sequence

<400> SEQUENCE: 42
wattwwtaaa wgwayaw                                                    17

<210> SEQ ID NO 43
<211> LENGTH: 190
<212> TYPE: DNA
<213> ORGANISM: Arabidopsis thaliana
<220> FEATURE:
<221> NAME/KEY: misc_feature
<222> LOCATION: (18)..(21)
<223> OTHER INFORMATION: n is a, c, g, or t
<220> FEATURE:
<221> NAME/KEY: misc_feature
<222> LOCATION: (97)..(131)
<223> OTHER INFORMATION: n is a, c, g, or t
<220> FEATURE:
<221> NAME/KEY: misc_feature
<222> LOCATION: (147)..(154)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (188)..(190)
<223> OTHER INFORMATION: n is a, c, g, or t

<400> SEQUENCE: 43
```

-continued

```
caaaaattaa taacagannn ntgtattttt aaaatttaat atttaatacc attatttcat      60
aatttattat acttttatta attttgtaat tattggnnnn nnnnnnnnnn nnnnnnnnnn     120
nnnnnnnnnn ntcgatatat atacgcnnnn nnnnagaaaa cacttagctc anattctctc     180 actttctnnn                                                            190

<210> SEQ ID NO 44
<211> LENGTH: 211
<212> TYPE: DNA
<213> ORGANISM: Arabidopsis thaliana
<220> FEATURE:
<221> NAME/KEY: misc_feature
<222> LOCATION: (16)..(61)
<223> OTHER INFORMATION: n is a, c, g, or t
<220> FEATURE:
<221> NAME/KEY: misc_feature
<222> LOCATION: (77)..(161)
<223> OTHER INFORMATION: n is a, c, g, or t

<400> SEQUENCE: 44
attctaaaat ttccannnnn nnnnnnnnnn nnnnnnnnnn nnnnnnnnnn nnnnnnnnnn      60
naaaaactta gagaagnnnn nnnnnnnnnn nnnnnnnnnn nnnnnnnnnn nnnnnnnnnn     120
nnnnnnnnnn nnnnnnnnnn nnnnnnnnnn nnnnnnnnnn ntagatgatt atttttaaat    180
gaacattaaa gaaaaactat tatatatata c                                   211

<210> SEQ ID NO 45
<211> LENGTH: 157
<212> TYPE: DNA
<213> ORGANISM: Glycine max
<220> FEATURE:
<221> NAME/KEY: misc_feature
<222> LOCATION: (16)..(37)
<223> OTHER INFORMATION: n is a, c, g, or t
<220> FEATURE:
<221> NAME/KEY: misc_feature
<222> LOCATION: (49)..(57)
<223> OTHER INFORMATION: n is a, c, g, or t
<220> FEATURE:
<221> NAME/KEY: misc_feature
<222> LOCATION: (75)..(81)
<223> OTHER INFORMATION: n is a, c, g, or t
<220> FEATURE:
<221> NAME/KEY: misc_feature
<222> LOCATION: (97)..(124)
<223> OTHER INFORMATION: n is a, c, g, or t
<220> FEATURE:
<221> NAME/KEY: misc_feature
<222> LOCATION: (136)..(139)
<223> OTHER INFORMATION: n is a, c, g, or t

<400> SEQUENCE: 45
tttctataag tttctnnnnn nnnnnnnnnn nnnnnnnaat attattacnn nnnnnnngcg      60
tctaacagta gtccnnnnnn nctgctataa atagagnnnn nnnnnnnnnn nnnnnnnnn     120 nnnnaaaatt attcannnnt tctaagttct aattttc                             157
```